(12) United States Patent
Japuntich et al.

(10) Patent No.: US 7,980,408 B2
(45) Date of Patent: Jul. 19, 2011

(54) DISPOSABLE CONTAINER SYSTEM AND METHOD WITH REUSABLE HOOD ASSEMBLY

(75) Inventors: John C. Japuntich, Harvard, IL (US); Mark Brian Finnestad, Huntley, IL (US); Anton M. Smudde, Elk Grove Village, IL (US)

(73) Assignee: Covidien AG (CH)

( * ) Notice: Subject to any disclaimer, the term of this patent is extended or adjusted under 35 U.S.C. 154(b) by 64 days.

(21) Appl. No.: 12/355,928

(22) Filed: Jan. 19, 2009

(65) Prior Publication Data

US 2009/0120821 A1 May 14, 2009

Related U.S. Application Data

(62) Division of application No. 11/523,211, filed on Sep. 19, 2006, now Pat. No. 7,596,844.

(51) Int. Cl.
*B65D 43/20* (2006.01)
*B65D 51/18* (2006.01)
*B65D 43/14* (2006.01)

(52) U.S. Cl. ............. 220/254.1; 206/366; 220/23.87; 220/254.3; 220/345.1; 220/908.3

(58) Field of Classification Search ............. 220/254.1, 220/23.4, 23.88, 23.87, 524, 252, 908.3, 220/909, 345.5, 254.3, 345.1; 206/366
See application file for complete search history.

(56) References Cited

U.S. PATENT DOCUMENTS

| 3,893,615 | A | * | 7/1975 | Johnson ...................... 232/43.2 |
|---|---|---|---|---|
| 4,663,122 | A | | 5/1987 | Sparks |
| 4,715,498 | A | | 12/1987 | Hanifl |
| 4,744,614 | A | * | 5/1988 | Gombosi ...................... 312/242 |
| 5,080,251 | A | | 1/1992 | Noack |
| 5,328,028 | A | | 7/1994 | Hale et al. |
| 5,413,757 | A | | 5/1995 | Kutner et al. |
| 5,415,315 | A | | 5/1995 | Ramirez |
| 5,419,435 | A | | 5/1995 | Perzan et al. |
| 5,494,186 | A | | 2/1996 | Marsh |
| 5,686,045 | A | | 11/1997 | Carter |
| 6,250,465 | B1 | | 6/2001 | Daniels et al. |
| 6,283,909 | B1 | | 9/2001 | Sharp |
| 7,143,905 | B2 | * | 12/2006 | Enayati et al. .............. 220/23.88 |
| 2002/0100706 | A1 | | 8/2002 | Sherman et al. |
| 2005/0169796 | A1 | | 8/2005 | Krakers et al. |
| 2006/0243619 | A1 | * | 11/2006 | Brown et al. ................. 206/366 |

OTHER PUBLICATIONS

Communication relating to the results of the Partial International Search Report for International Application No. PCT/US2007/020092 filed on Sep. 17, 2007.

* cited by examiner

*Primary Examiner* — Anthony Stashick
*Assistant Examiner* — Niki M Eloshway
(74) *Attorney, Agent, or Firm* — Lisa E. Winsor, Esq.

(57) ABSTRACT

A kit for medical waste disposal comprising a plurality of containers; a hood assembly configured to substantially cover an open end of a respective one said containers, the hood assembly defining a passage through which medical waste can be passed to the open end of said container; and a plurality of lids, separate from the hood assembly, each configured to be placed over an open end of a respective container and to substantially close the open end of said container when said container is at least partially filled with medical waste; each of said containers being configured for separation from the hood assembly for disposal.

16 Claims, 20 Drawing Sheets

DISPOSABLE CONTAINER SYSTEM AND METHOD WITH REUSABLE HOOD ASSEMBLY

This application is a Divisional of application Ser. No. 11/523,211, filed Sep. 19, 2006.

BACKGROUND OF THE INVENTION

The present invention relates to a container system and method for medical waste disposal. More specifically, the present invention relates to a medical waste container system and method utilizing a disposable container and a reusable hood assembly.

Various types of containers for hospital use have been developed for receiving medical waste in a surgical operating room, pre-op or post-op room, a patient's room, or in other clinical or non-clinical settings in which medical waste is generated. These containers are particularly designed to protect the user of such containers, such as doctors, nurses, or other hospital personnel, from the hospital waste products that may be disposed therein. Such hospital waste products might include surgical sharps, such as needles, syringes, scalpel blades, or the like, or might include gauzes, bandages, or sponges. It is important to prevent the user of a sharps container from being accidentally cut or punctured by its contents. Furthermore, it is important to prevent access to the contents of the container during disposal thereof. Additionally, it is important for the containers to be maintained sterile to prevent contamination, infection or the like from the container assembly itself.

Examples of sharps disposal containers include those shown in U.S. Pat. No. 4,715,498, entitled "Sharps Disposal System"; U.S. Pat. No. 5,080,251, entitled "Tortuous Path In-Patient Room Medical Waste Disposal Container"; and U.S. Pat. No. 5,494,186, entitled "Wall Mounted Medical Waste Disposal Container With Pivoted Top Closure Lid", each of which is incorporated herein by reference.

Referring to FIGS. 1 and 2, a sharps disposal container system 10 similar to that described in U.S. Pat. No. 5,494,186 is shown. The disposable container system 10 includes a disposable container 12 upon which a hood assembly 11 is permanently mounted. As seen in FIG. 2, the hood assembly 11 includes locking tabs 17 about its lower periphery that are configured to lock in corresponding locking holes (not shown) in the rim of the container 12. The hood assembly 11 includes opposed cowl surfaces 13 and 15 that define a tortuous path opening 20 through the hood assembly 11 into the disposable container 12. The tortuous path opening 20 reduces accessibility to disposed articles within the container 12. Once the container 12 is filled to a desired level, the pivotal lid 14 is moved from the illustrated position to a closed position wherein the lid 14 covers the opening 20 and the lid locking tab 16 engages locking slot 18 to permanently lock the lid 14 in this closed position. The disposable container system 10 is sealed and ready for disposal, with the container 12 and permanently connected hood assembly 11 being removed and send for disposal.

Referring to FIGS. 3 and 4, a sharps disposal container system 22 similar to that described in U.S. Pat. No. 4,715,498 is shown. Primary components of the system 22 are a hollow, outer enclosure 34 and an inner container system 23 shaped to be located within the outer enclosure 34. The inner container system 23 is similar to the container system 10 of FIGS. 1 and 2 and includes a disposable container 24 and a permanently attached hood assembly 26. As best shown in FIG. 4, the container 24 includes a peripheral, outwardly-extending flange 25 and the hood assembly 26 includes a skirt having an inwardly-extending lip 27 which snaps beneath the flange 25 when the hood assembly 26 is placed on the container 24. The hood assembly 26 includes a pivotal closure 28 installed within an inlet 29 formed therein. The pivotal closure 28 includes an upwardly-extending leg 30 which in a closed position, as shown in FIG. 4, closes the inlet 29 and a downwardly-depending leg 32 which extends into the interior of the inner container 24 and which pivots to a position which blocks the inlet 29 and minimizes accessibility to the contents of the container when the closure 28 is moved to an open, sharps receiving position (as shown in phantom in FIG. 4).

Turning to the outer enclosure 34, the enclosure 34 includes an access door 36 secured by hinges 35 onto the main body 38 of the enclosure 34. Opposite the hinges 35, the door 36 includes a lock 37 to lock the door 36. The main body 38 of the outer enclosure 34 includes a raised cowl 40 extending over a slot 42. The inner container system 23 is positional in the enclosure 34 such that the hood assembly 26 is within the cowl 40 with the inlet 29 aligned with the slot 42.

When the inner container 24 has been filled with sharps, it is preferably discarded. In order to secure the contents therewithin, a plurality of catches or locks 46 are formed in the interior of the hood 26. By applying pressure to the face of the closure 28, the closure 28 is forced within the hood 26 and snaps past the first or both of the catches 46. Due to the configuration of the catches 46, the closure 28 may be pivoted past the catches toward the interior of the hood 26, but is prevented from returning. The contents of the container 24 are therefore secured. The enclosure door 36 is opened and the inner container system 23, including the container 24 and the hood assembly 26 permanently attached thereto, is removed and discarded.

Disposal of the filled containers adds to land fill waste and adds to the cost of the disposable container system. Accordingly, there remains a need for an improved container system that can be employed to decrease the waste and cost associated with prior art systems.

SUMMARY OF THE INVENTION

In view of the forgoing, it is desirable to provide a disposable container system wherein the hood assembly can be reused while maintaining desired safety and sanitization levels. At least one of these objectives is achieved by a method of medical waste disposal comprising (a) positioning an open end of a container relative to a hood assembly such that the hood assembly substantially covers the open end of the container; (b) depositing medical waste in the container through a passage defined by the hood assembly until the container is at least partially full; (c) placing a lid over the open end of the container such that the open end is substantially closed; (d) disposing of the container; (e) sterilizing the hood assembly; and (f) repeating step (a).

DETAILED DESCRIPTION OF THE INVENTION

Figure 1:
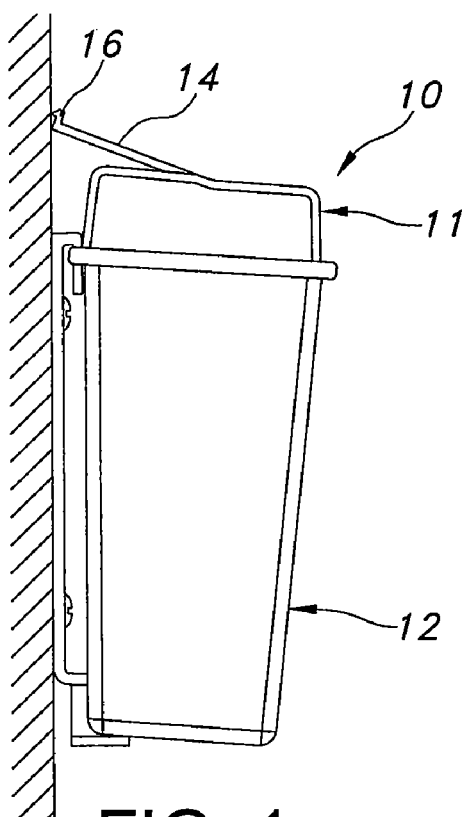
FIG. 1 is a side elevation view of a prior art medical waste disposal system.

Although the invention is illustrated and described herein with reference to specific embodiments, the invention is not intended to be limited to the details shown. Rather, various modifications may be made in the details within the scope and range of equivalents of the claims and without departing from the invention.

Referring to FIGS. 5, 6 and 8-10, a medical waste disposal system 50 in accordance with a first embodiment will be described. The medical waste disposal system 50 generally comprises a disposable container 51, a deck component 60, a hood assembly 70 and a lid 80. The disposable container 51 includes a wall structure 52 that defines an open end 53 with a rim 54 thereabout. The disposable container 51 is configured to receive medical waste, including sharps and the like, and may have various configurations of the wall structure 52 and the rim 54 other than the illustrated structure.

Figure 6:
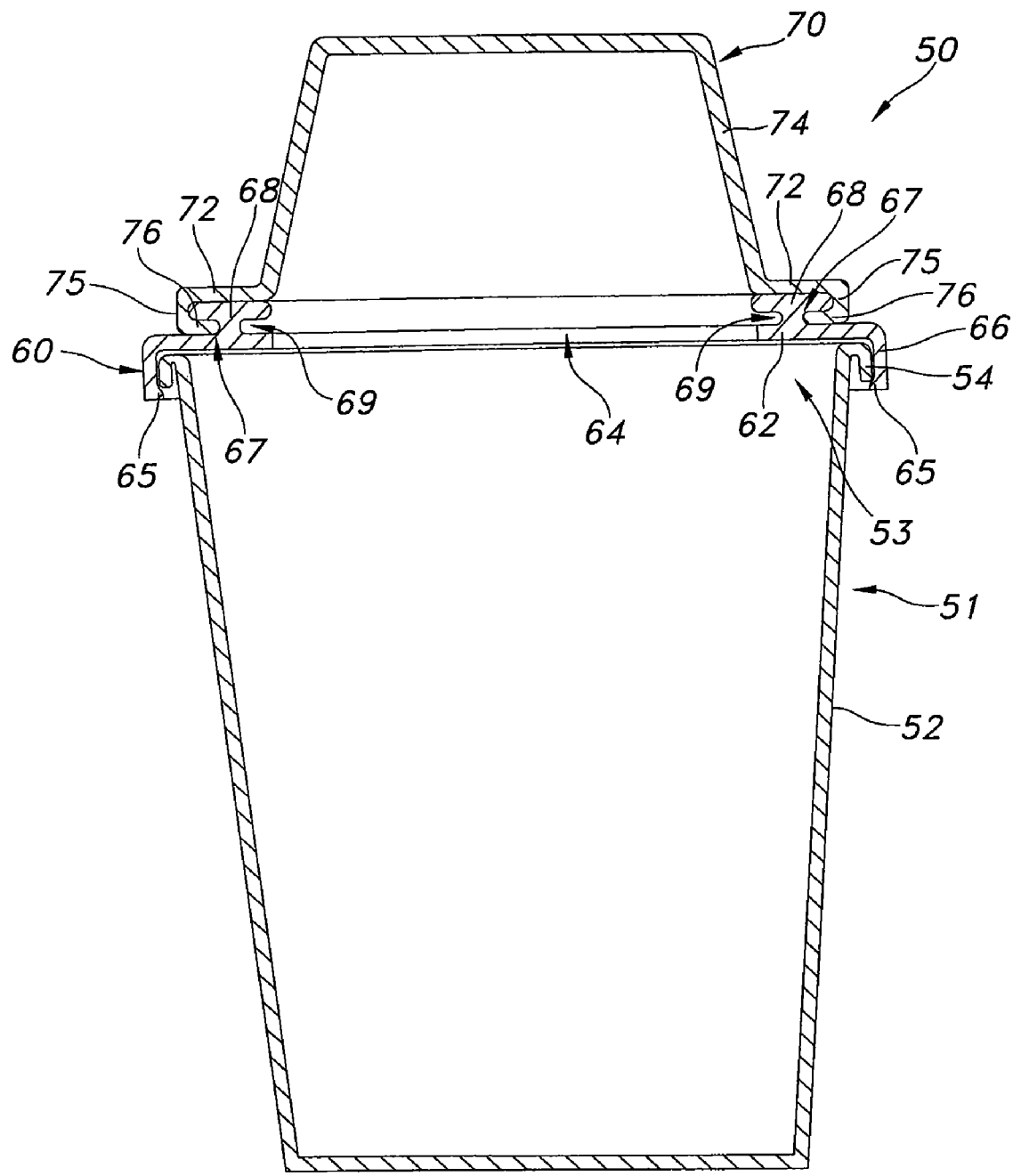
FIG. 6 is a front cross-sectional view of the medical waste disposal system of FIG. 5 with the hood assembly, having the pivotal closure removed for clarity, positioned on the disposable container.

The deck component 60 includes a deck surface 62 that substantially covers the open end 53 of the disposable container 51, except for an opening 64 through the deck surface 62. The deck component 60 is preferably permanently attached to the disposable container 51, but may be removably attached, if desired. In the present embodiment, a skirt 66 depends from the deck surface 62 and is configured to fit about the rim 54 of the disposable container 51 and attach thereto. The skirt 66 includes a series of inward projections 65, as shown in FIG. 6, spaced about its perimeter. The projections 65 engage the underside of the rim 54 to attach the deck component 60 to the disposable container 51. Other means for securing the deck component 60 to the disposable container 51 may also be utilized. For example, the skirt 66 may be provided with a continuous internal protrusion that engages the rim 54. Alternatively, a series of locking tabs (not shown) may project downwardly from the deck surface 62 and snap-fit into corresponding locking holes (not shown) positioned about the rim 54 of the disposable container 51, with or without the skirt 66. Other attachment mechanisms, for example, mechanical fasteners, adhesives, bonding methods or welding methods, may also be used. Alternatively, the deck component 60 may be formed integrally with the disposable container 51.

The deck component 60 defines first and second connectors. The first connector is configured to removably secure the hood assembly 70 to the deck component 60 and the second connector is configured to secure the lid 80 over the opening 64 through the deck surface 62. In the present embodiment, the first and second connectors are defined by a pair of t-shaped bars 68 extending from the deck surface 62 on opposite sides of the opening 64. Each t-shaped bar 68 defines an outer track 67 and an inner track 69 between the bar 68 and the deck surface 62. The pair of outer tracks 67 are configured to slidably receive the hood assembly 70, as will be described hereinafter, and thereby provide the first connector. The pair of inner tracks 69 are configured to slidably receive the lid 80, as will be described hereinafter, and thereby provide the second connector.

Figure 5:
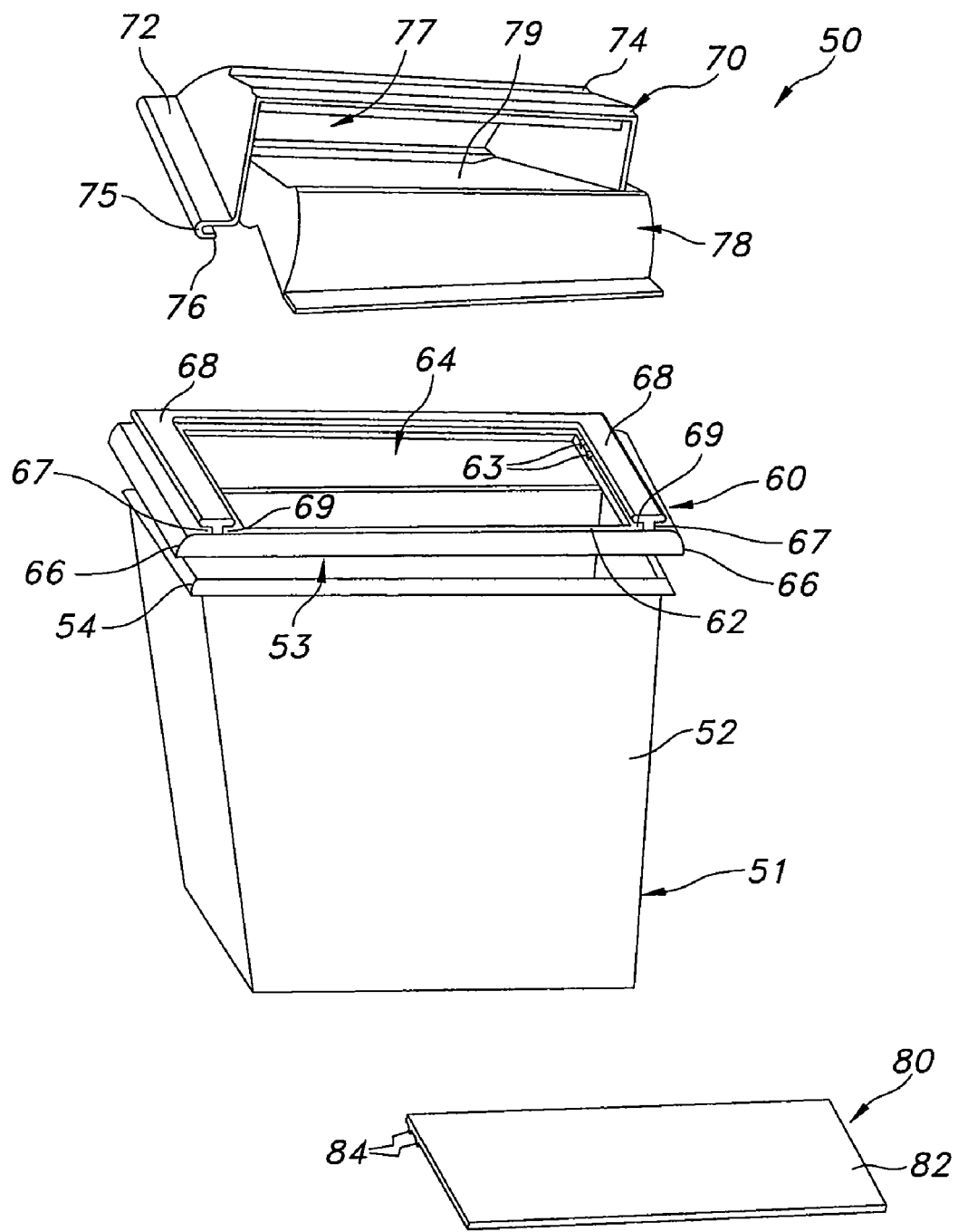
FIG. 5 is an exploded perspective view of a first exemplary embodiment of a medical waste disposal system according to aspects of this invention.
Figure 8:
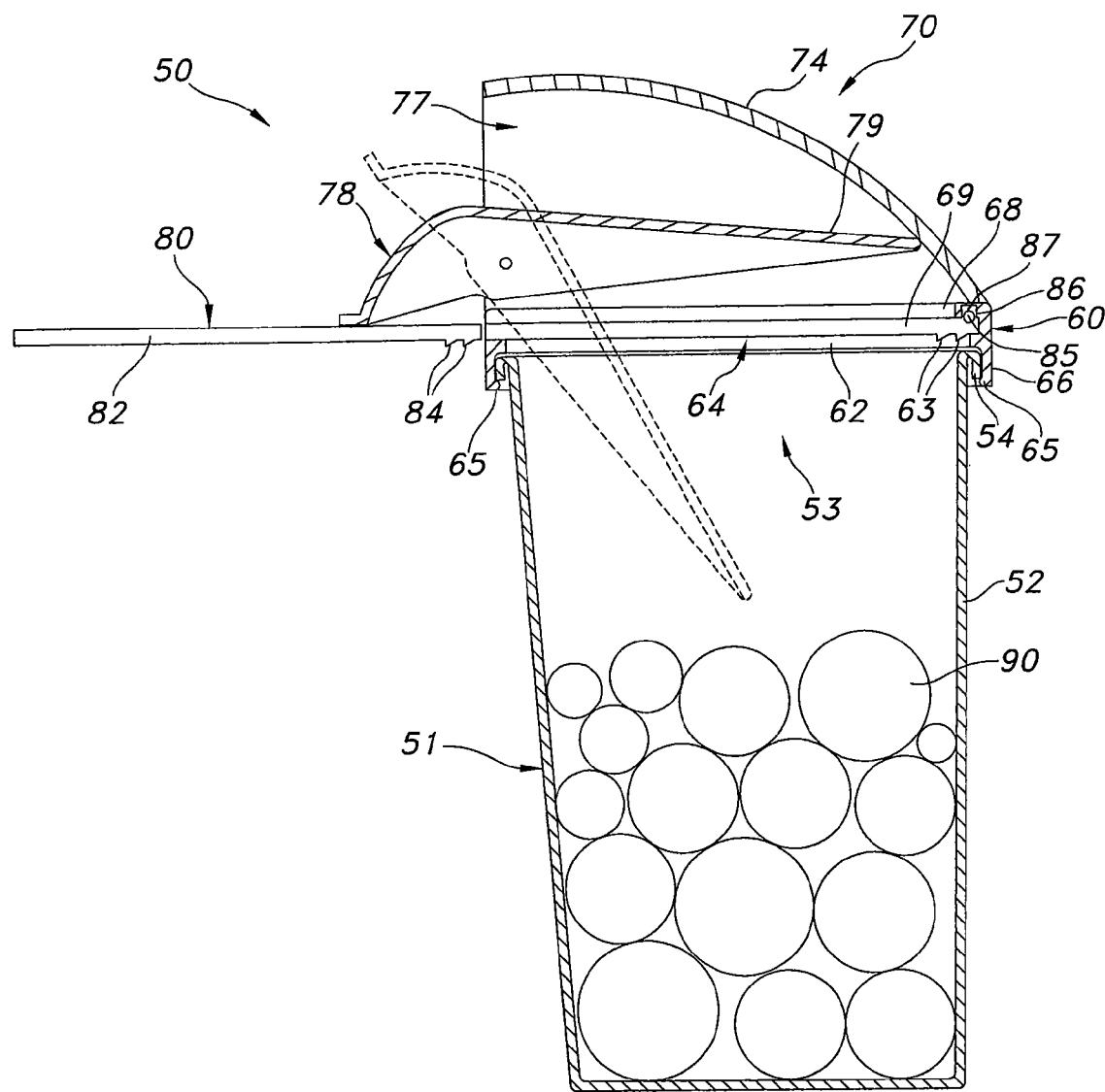
FIG. 8 is a side cross-sectional view of the medical waste disposal system of FIG. 5.

Referring to FIGS. 5, 6 and 8, the hood assembly 70 includes a raised cowl 74 extending from a hood platform 72. The cowl 74 defines an open passage 77 therethrough. The hood assembly 70 functions to minimize access into the disposable container 51. The hood assembly 70 is configured to facilitate the passage of various medical waste into the disposable container 51, but limit the ability for an individual to reach into the disposable container and remove or otherwise contact any previously disposed materials. In the present embodiment, a pivotal closure 78 is pivotally supported by the cowl 74 and has a closure surface 79 that is moveable between a closed position, as shown in FIG. 8, in which the surface 79 substantially closes the passage 77, and an open position, as shown in phantom in FIG. 8, in which sharps 90 or the like may pass through the passage 77, through the opening 64 and into the disposable receptacle 51.

Figure 2:
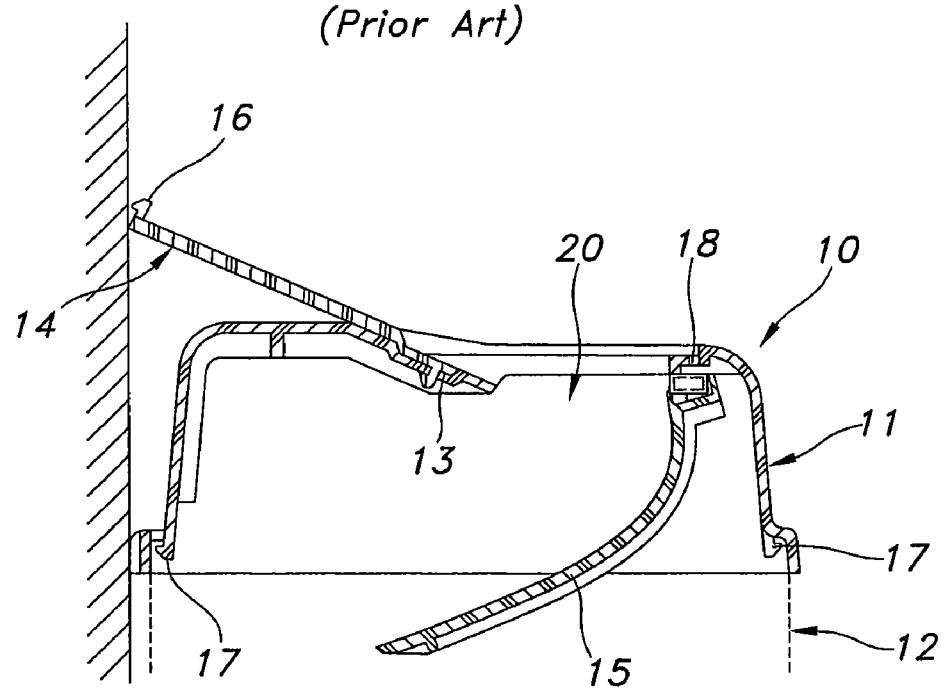
FIG. 2 is a cross-sectional view through the hood assembly of the medical waste disposal system of FIG. 1.
Figure 3:
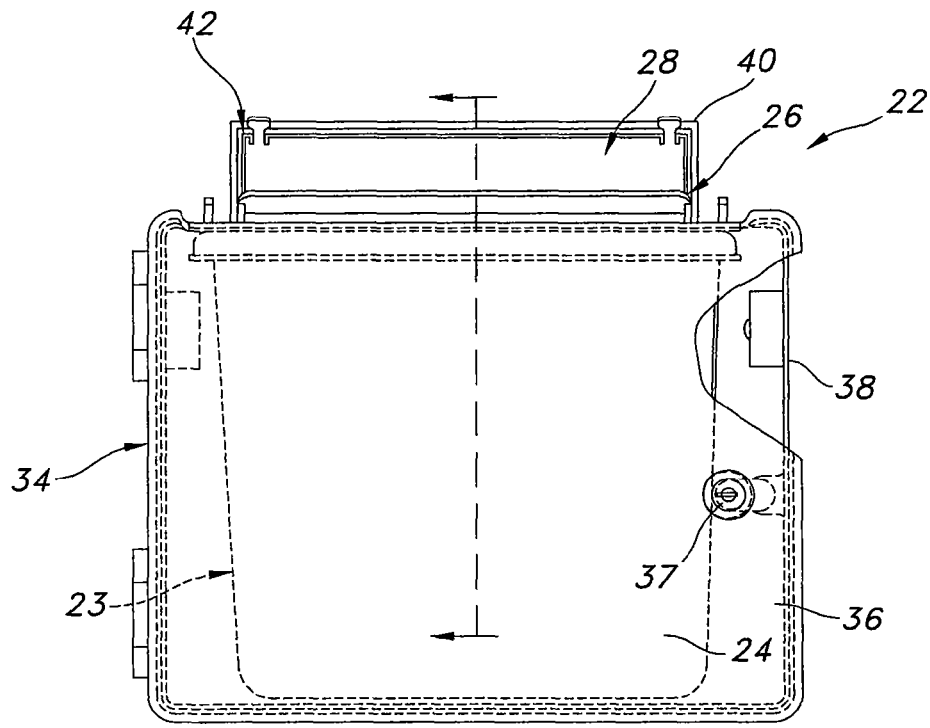
FIG. 3 is a front elevation view of another prior art medical waste disposal system.
Figure 4:
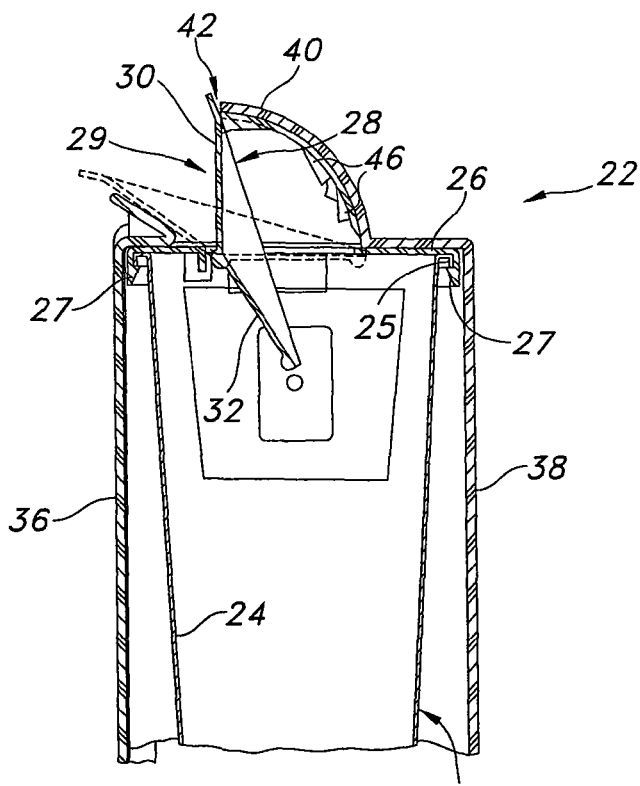
FIG. 4 is a cross-sectional view through the medical waste disposal system of FIG. 3.
Figure 7:
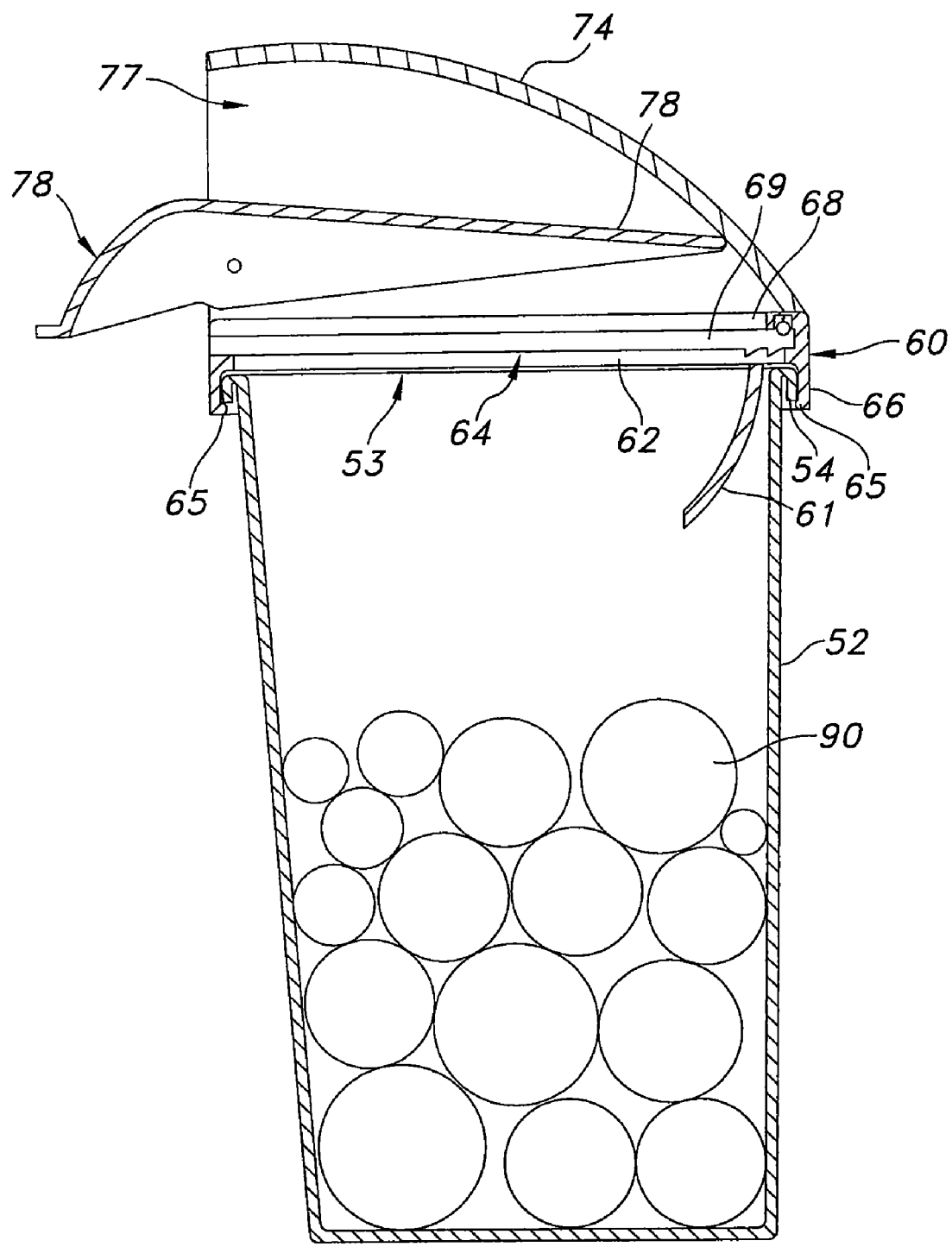
FIG. 7 is a side cross-sectional view illustrating a medical waste disposal system that is an alternative exemplary embodiment.

While a pivotal closure 78 is illustrated in the present embodiment, the hood assembly 70 may include other means for limiting access through the passage 77. For example, the hood assembly 77 may include one or more fixed surfaces, similar to those shown in FIG. 2, which limit access through the passage 77 or otherwise define a tortuous or non-direct path through the passage 77 into the disposable container 51. In the alternative embodiment shown in FIG. 7, access into the disposable container 51 is further limited by a fixed cowl surface 61 extending downwardly from the deck surface 62.

The fixed cowl surface 61 is below the deck surface 62 and the tracks 69, and therefore, will not interfere with positioning of the lid 80, as will be described hereinafter with respect to the first embodiment.

Referring to FIGS. 5 and 6, a leg 75 extends downward from each lateral edge of the hood platform 72. A respective flange 76 extends inward from each leg 75 such that each flange 76 is substantially parallel to the hood platform 72. The flanges 76 are configured to be received in respective ones of the outer tracks 67. To assemble the medical waste disposal system 50, the hood assembly 70 is slid onto the deck component 60 with the flanges 76 being received in the outer tracks 67.

Figure 9:
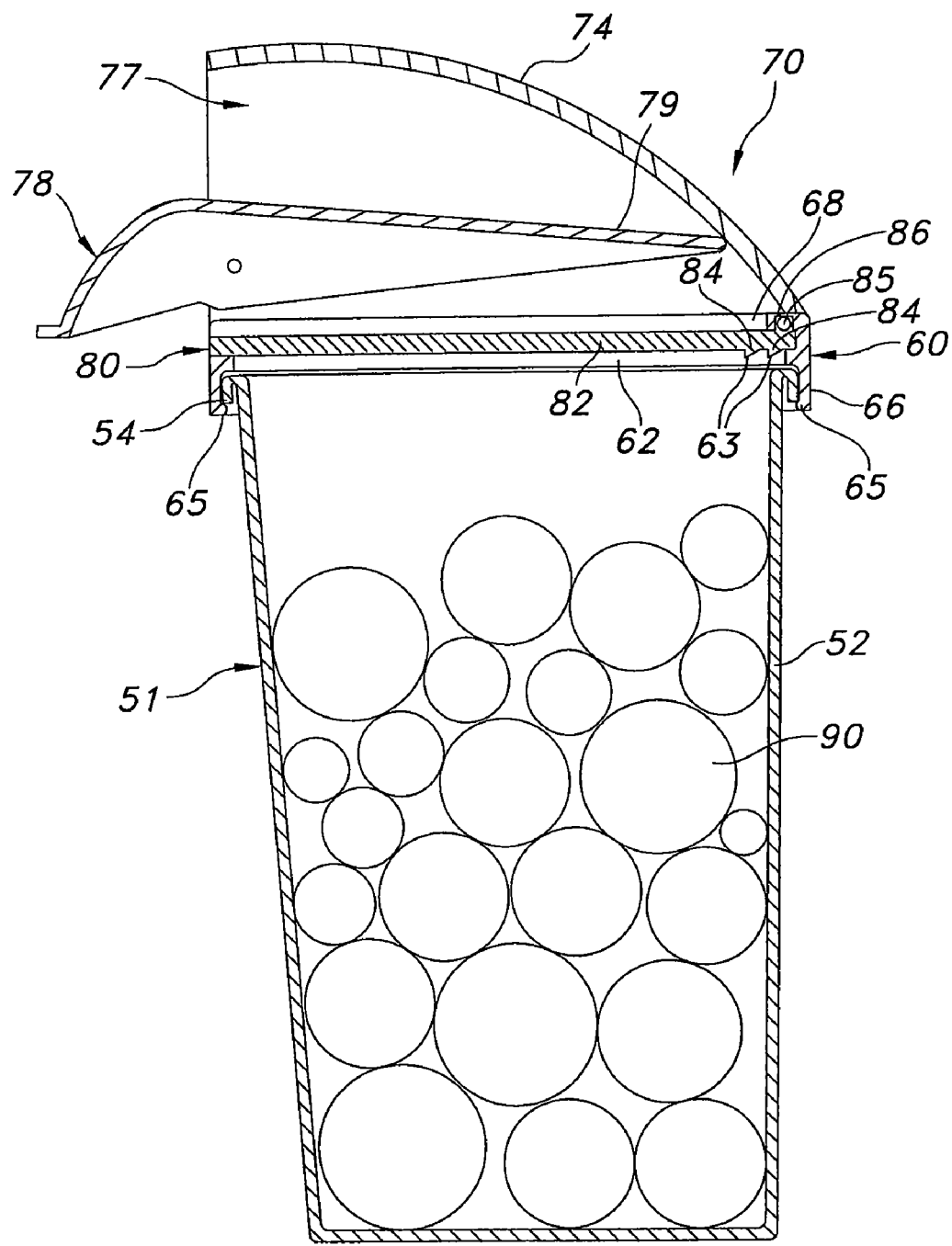
FIG. 9 is a side cross-sectional view similar to FIG. 8 illustrating a lid positioned over the open end of the disposable container.
Figure 10:
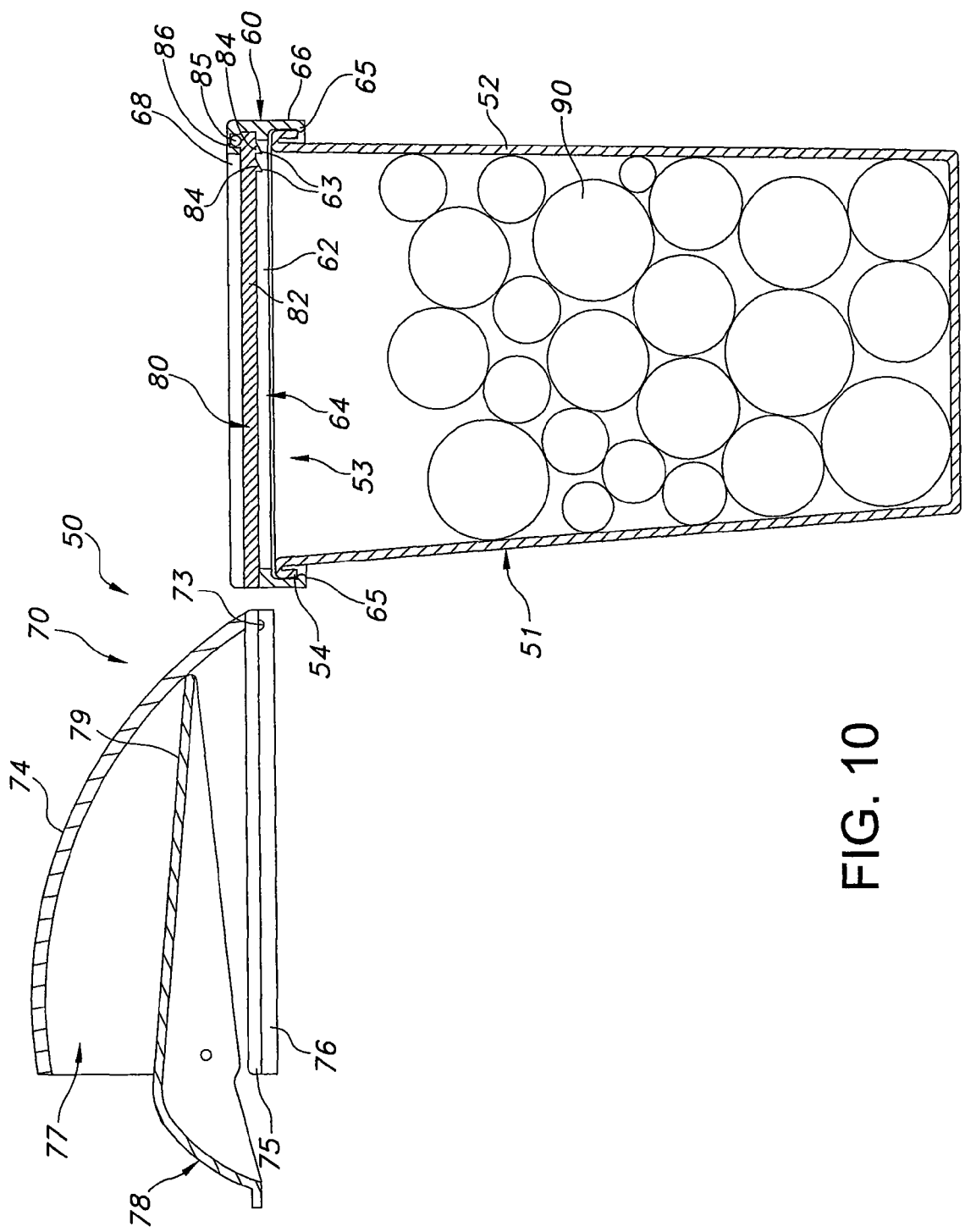
FIG. 10 is a side cross-sectional view similar to FIG. 8 illustrating the hood assembly removed from the disposable container.

The hood assembly 70 is preferably secured relative to the deck component 60 such that it can only be removed by authorized personnel, for example, via a keyed latch, or only be removed once the lid 80 is positioned to cover the opening 64. Referring to FIGS. 8-10, the present invention utilizes a biased locking rod 85 to retain the hood assembly 70 until the lid 80 is positioned over the opening 64. The rod 85 extends laterally in a groove 86 in the t-bar 68 such that the ends of the rod 85 extend laterally to both tracks 67 and 69. The rod 85 may be provided on one of the t-bars 68 or both of them. The rod 85 is biased by a spring 87 or the like to a locking position, see FIG. 8, in which a portion of the rod 85 occupies an area in each track 67 and 69. The respective hood assembly flange 76 has a corresponding notch 73, such that when the flange 76 is slid into the track 67, the biased rod 85 is received in the notch 73 and locks the hood assembly 70 to the deck component 60. To disengage the hood assembly 70, the lid 80 must be positioned in the inner tracks 69. As the lid 80 moves into the inner tracks 69, the lid body 82 contacts the portion of the rod 85 extending into the track 69 and forces the rod 85 upward against the force of the spring 87, as shown in FIG. 9. Upward movement of the rod 85 causes the rod 85 to disengage from the hood assembly notch 73, thereby releasing the hood assembly 70 for sliding removal from the deck component 60, as shown in FIG. 10.

Referring to FIGS. 8-10, operation of the medical waste disposal container 50 will be described. The hood assembly flanges 76 are slid into the respective outer tracks 67 such that the hood assembly 70 covers the deck opening 64, thereby limiting access into the disposable container 51. The medical waste disposal system 50 is ready for use and sharps 90 or the like may be disposed in the disposable container 51 by placing the items into the hood passage 77 and pivoting the pivotal closure 78, either manually or automatically due to the weight of the item, as illustrated in FIG. 8.

Once the disposable container 51 is filled to a given level, the lid 80 is used to cover and substantially seal the opening 64 in the deck component 60. Referring to FIGS. 5 and 9, the lid 80 includes a planar body 82 with a length equal to the distance defined by the two inner tracks 69 and a width at least as large as the width of the opening 64. The lid 80 is preferably provided with a locking mechanism that will prevent removal of the lid 80 from the deck component 60 once the lid 80 has been installed. In the present embodiment, a pair of barbs 84 extend downward from the planar body 82 along each lateral edge thereof. The barbs 84 are configured to engage corresponding notches 63 provided along each inner track 69. The barbs 84 and notches 63 are preferably sloped such that the lid 80 is easily inserted into the tracks 69, but difficult to remove. As can be seen in FIGS. 6 and 9, since the hood assembly 70 does not interfere with the tracks 69 and the pivotal closure 78 is above the opening 64, the lid 80 is positional over the opening 64 prior to removal of the hood assembly 70.

Referring to FIG. 10, after the lid 80 is positioned over the opening 64 and the contents are securely sealed within the disposable container 51, the hood assembly 70 is slidingly removed from the deck component 60. With the hood assembly 70 removed, the filled disposable container 51, with the deck component 60 and lid 80 attached thereto, is disposed of in a normal manner. The significant amount of material of the hood assembly 70 is not disposed of, but instead is reused, as described in more detail hereinafter. Reusing of the hood assembly 70 reduces the amount of waste and also reduces the manufacturing costs as a new receptacle 51 with a deck component 60 attached thereto can be used with the already manufactured hood assembly 70.

Figure 11:
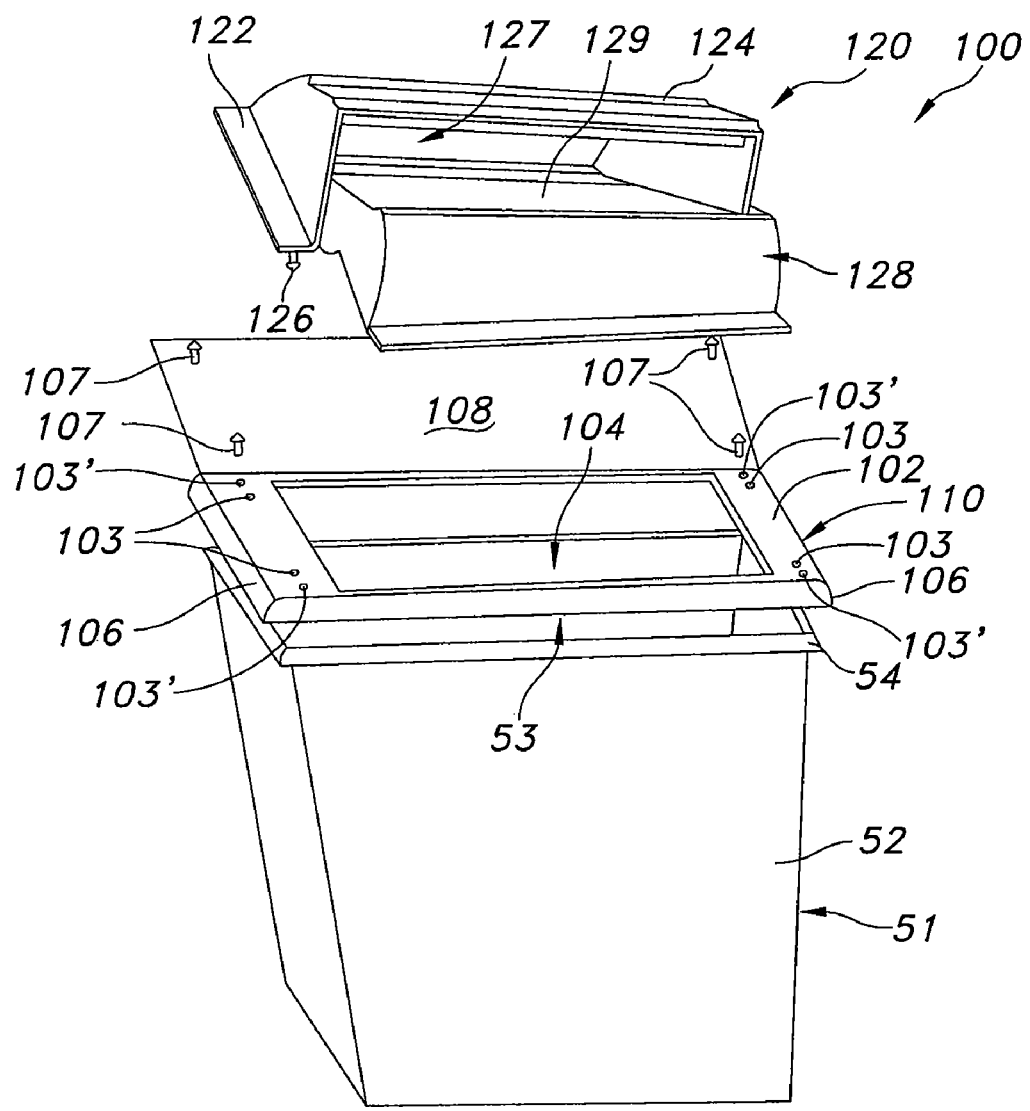
FIG. 11 is an exploded perspective view of a medical waste disposal system that is yet another alternative exemplary embodiment.
Figure 12:
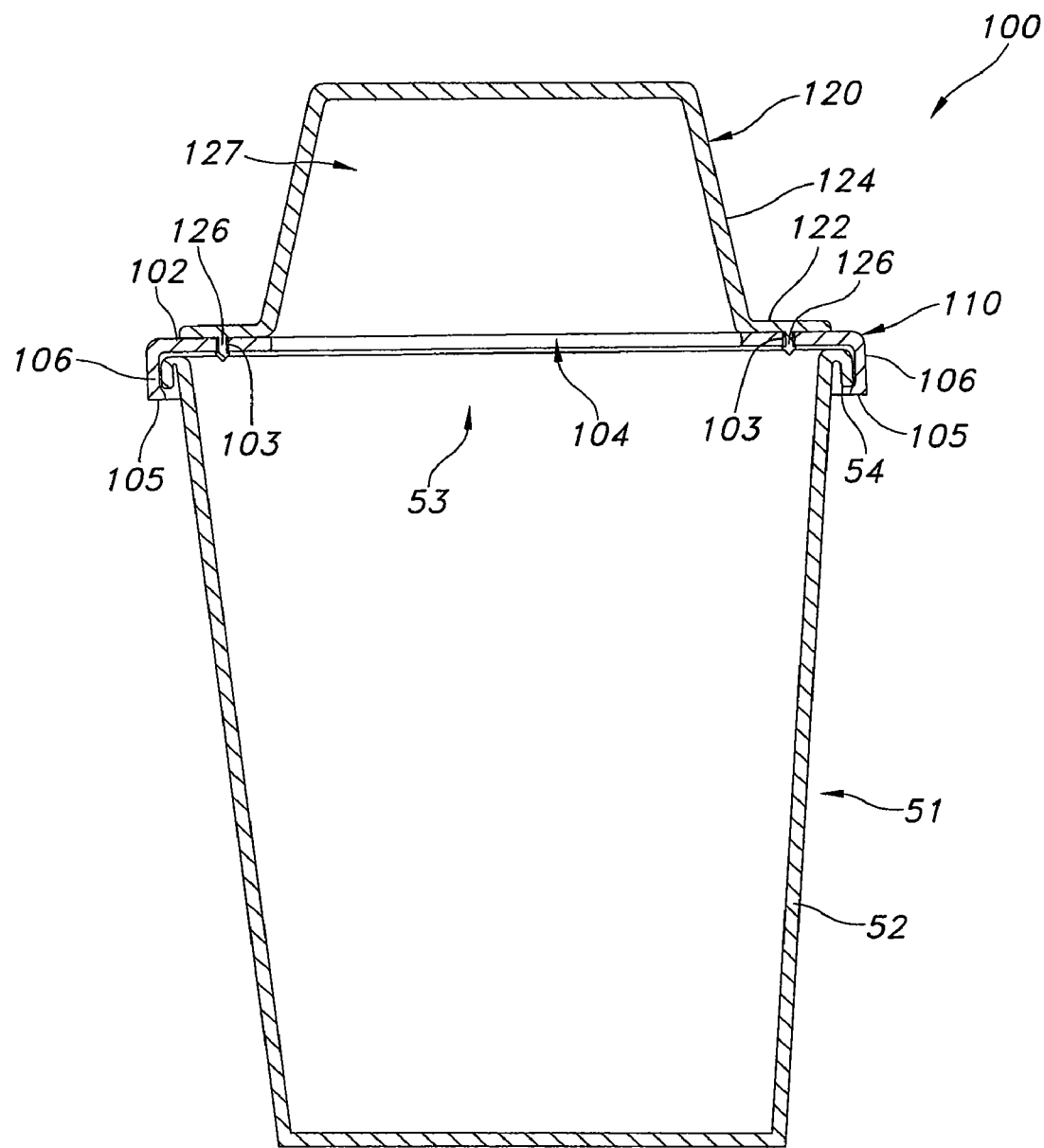
FIG. 12 is a front cross-sectional view of the medical waste disposal system of FIG. 11 with the hood assembly, having the pivotal closure removed for clarity, positioned on the disposable container.

Referring to FIGS. 11 and 12, a medical waste disposal system 100 in accordance with an alternative embodiment will be described. The medical waste disposal system 100 is similar to the previous embodiment and generally comprises a disposable container 51, a deck component 110, a hood assembly 120 and a lid 108. The disposable container 51 is the same as in the previous embodiment and includes a wall structure 52 that defines an open end 53 with a rim 54 thereabout. The disposable container 51 is configured to receive medical waste, including sharps and the like, and may have various configurations of the wall structure 52 and the rim 54 other than the illustrated structure.

The deck component 110 includes a deck surface 102 that substantially covers the open end 53 of the disposable container 51, except for an opening 104 through the deck surface 102. As in the previous embodiment, the deck component 110 is preferably permanently attached to the disposable container 51, but may be removably attached, if desired. A skirt 106 depends from the deck surface 102 and is configured to fit about the rim 54 of the disposable container 51 and attach thereto. The skirt 106 includes a series of inward projections 105, as shown in FIG. 12, spaced about its perimeter. The projections 105 engage the underside of the rim 54 to attach the deck component 110 to the disposable container 51. Other means for securing the deck component 110 to the disposable container 51 may also be utilized.

The deck component 110 of the present embodiment defines multiple connectors configured to secure both the hood assembly 120 and the lid 108. The connectors include first and second series of receiving openings 103 and 103' extending through the deck surface 102 and configured to receive complimentary locking tabs 126 and 107 extending from the hood assembly 120 and the lid 108, respectively. The connection features of the present embodiment simplify the deck component 110 design and further reduce the amount of material to be disposed.

Referring to FIG. 11, the hood assembly 120 is similar to the previous embodiment and includes a raised cowl 124 extending from a hood platform 122. The cowl 124 defines an open passage 127 therethrough. The hood assembly 120 again functions to minimize access into the disposable container 51. A pivotal closure 128 is pivotally supported by the cowl 124 and has a closure surface 129 that is moveable between a closed position and an open position, similar to the previous embodiment. While a pivotal closure 128 is illustrated in the present embodiment, the hood assembly 120 may include other means for limiting access through the passage 127, as explained above in conjunction with the previous embodiment.

To connect the hood assembly 120 to the deck component 110, a series of locking tabs 126 extend downward from the hood platform 122. As shown in FIG. 12, the locking tabs 126 are configured to be received in corresponding ones of the receiving openings 103 in the deck surface 102. The illustrated locking tabs 126 snap-fit into the receiving openings 103 and are removed therefrom by exerting an upward separation force. Other configurations may be also be utilized. For example, the locking tabs may be biased between a locking position and a non-locking position, with a special tool required to contact the locking tabs and move them to the non-locking position for removal of the hood assembly 120. Alternatively, the locking tabs may be rotatable between a locking position and a non-locking position and require a key or the like to rotate the locking tabs to the non-locking position.

Referring to FIG. 11, the lid 108 also includes a series of locking tabs 107 configured to be received in receiving openings 103' on the deck surface 102 of the deck component 110. The receiving openings 103' configured to receive the lid tabs 107 may be the same receiving openings 103 as those configured to receive the hood assembly locking tabs 126, or may be separate receiving openings 103' as indicated. The locking tabs 107 and the receiving openings 103' are configured such that the locking tabs 107 are received and not easily removed from the receiving openings 103'. In the present embodiment, the lid 108 is hingedly connected to the deck component 110 for easy access, but such is not required and the lid 108 may be manufactured as a separate component.

In operation, the hood assembly 120 is attached to the deck component 110 and the disposable container 51 is filled in a manner similar to that described in the previous embodiment. When the disposable container 51 is filled to a given level, the hood assembly 120 is removed from the deck component 110 as described above. After the hood assembly 120 is removed, the lid 108 is positioned over the opening 104 and the locking tabs 107 are engaged in the receiving openings 103'. Since removal of the hood assembly 120 exposes the opening 104, the present embodiment is preferably used in a minimum risk environment, for example, home use, or is secured, for example, in an external enclosure, such that only authorized personnel may remove the hood assembly 120.

Once the hood assembly 120 is removed, the filled disposable container 51, with the deck component 110 and lid 108 attached thereto, is disposed of in a normal manner. The significant amount of material of the hood assembly 120 is not disposed of, but instead is reused, as described in more detail hereinafter. Again, reusing of the hood assembly 120 reduces the amount of waste and also reduces the manufacturing costs as a new receptacle 51 with a deck component 110 attached thereto can be used with the already manufactured hood assembly 120.

Figure 13:
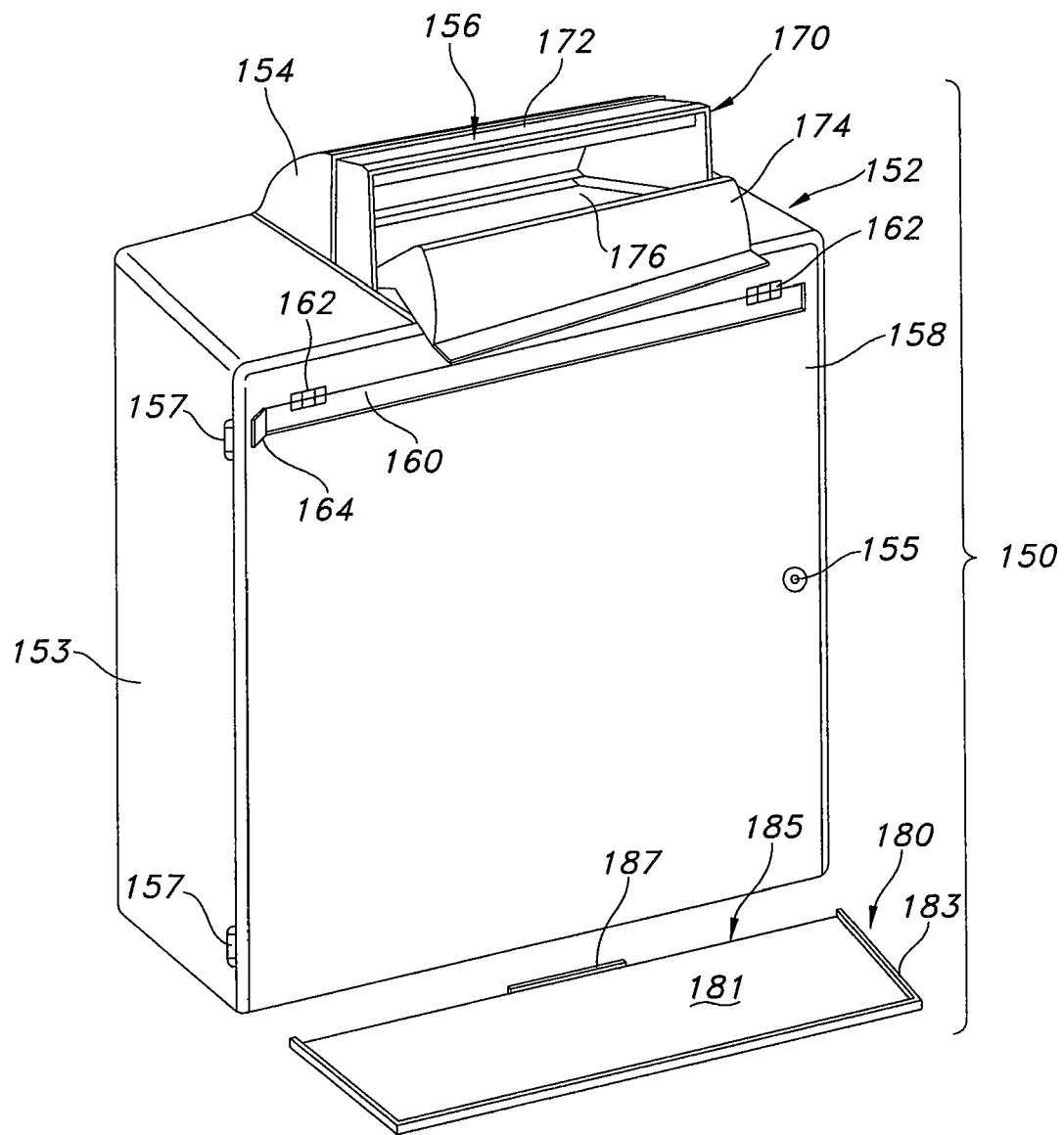
FIG. 13 is an isometric view of a medical waste disposal system that is still another alternative exemplary embodiment.
Figure 14:
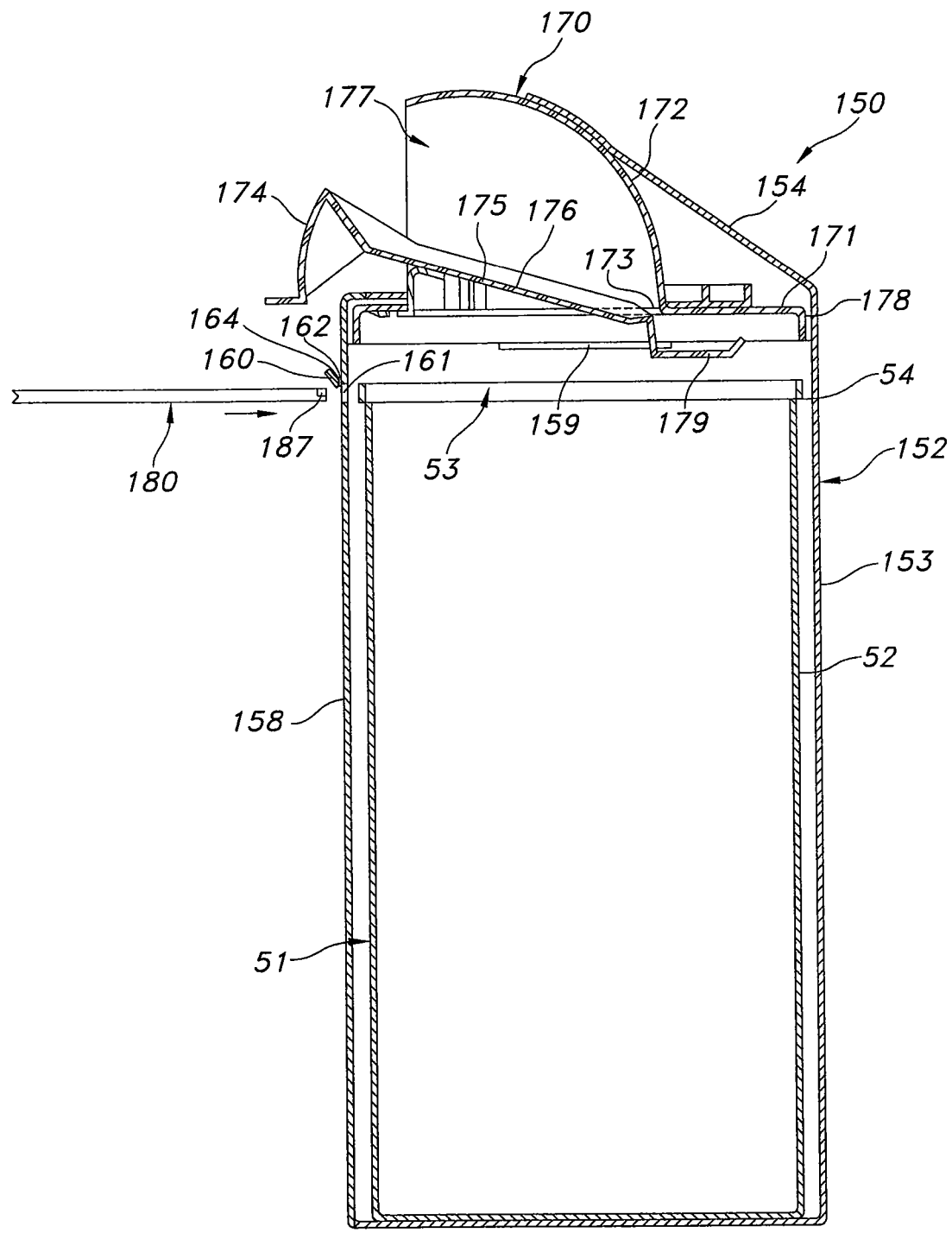
FIG. 14 is a side cross-sectional view of the medical waste disposal system of FIG. 13.
Figure 15:
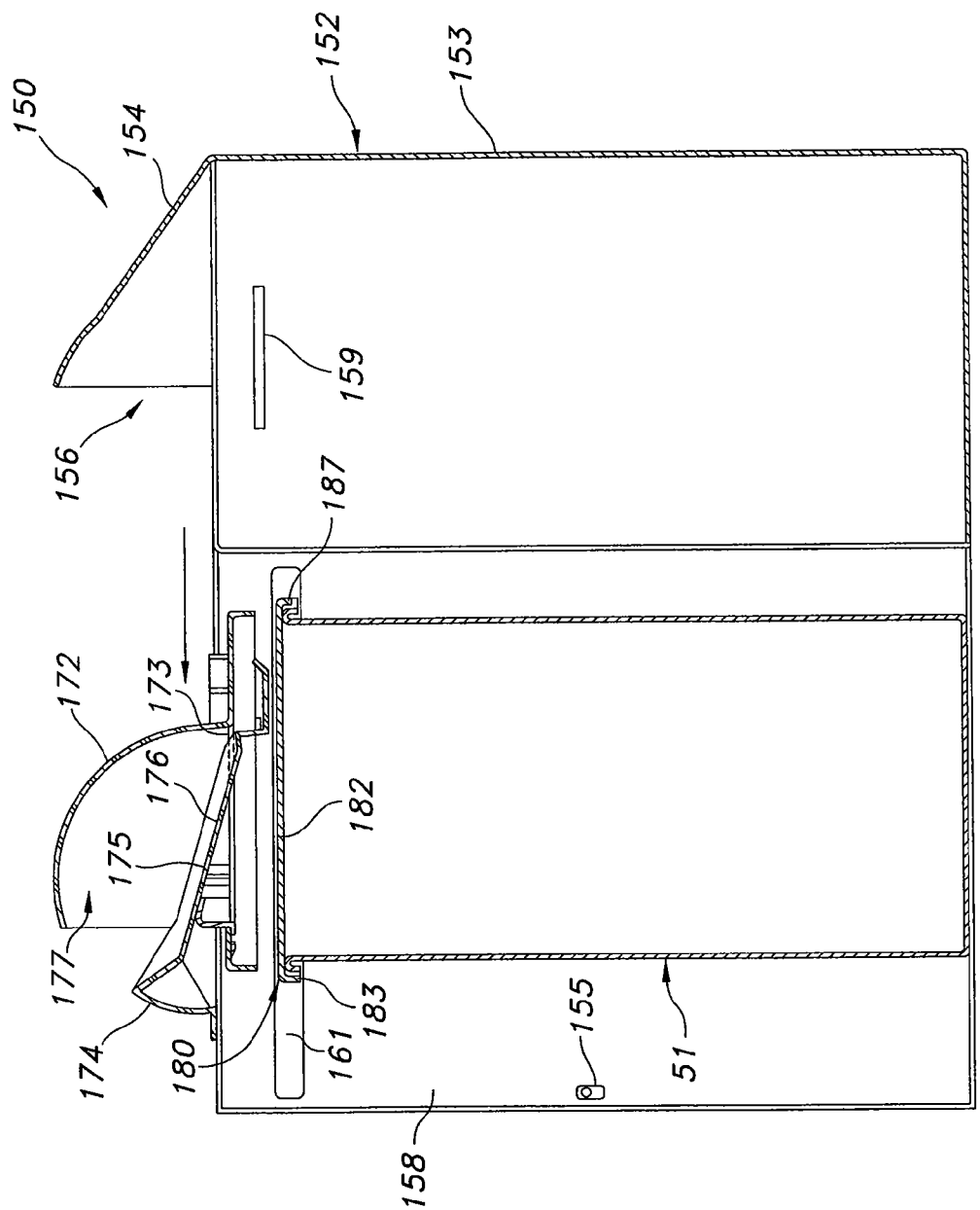
FIG. 15 is a side cross-sectional view similar to FIG. 14 with the enclosure door open and the hood assembly and covered disposable container removed therefrom.

Referring to FIGS. 13-15, a medical waste disposal system 150 in accordance with another alternative embodiment will be described. The system 150 generally comprises a hollow, outer enclosure 152, a disposable container 51 configured to be located within the outer enclosure 152, and a reusable hood assembly 170. The disposable container 51 is substantially the same as in the previous embodiments and includes a wall structure 52 that defines an open end 53 with a rim 54 thereabout. The disposable container 51 is configured to receive medical waste, including sharps and the like, and may have various configurations of the wall structure 52 and the rim 54 other than the illustrated structure.

Turning to the outer enclosure 152, the enclosure 152 includes an access door 158 secured by hinges 157 onto the main body 153 of the enclosure 152. Opposite the hinges 157, the door 158 includes a lock 155 to lock the door 158 in a closed position relative to the main body 153. The main body 153 of the outer enclosure 152 includes a raised cowl 154 extending over a slot 156. The disposable container 51 is positioned in the main body 153 and retained by the door 158.

The hood assembly 170 is removably supported by the main body 153, as will be described in more detail hereinafter, with the hood assembly passage 177 aligned with the slot 156 and defining a tortuous path or the like through the hood assembly 170 into the disposable container 51. While the outer enclosure 152 is illustrated with an external raised cowl 154, such is not required as the hood assembly cowl 172 may provide the only cowl with the top surface of the enclosure 152 being substantially flat.

Referring to FIG. 14, the hood assembly 170 includes a hood platform 171 with a opening 173 therethrough. A raised cowl 172 extends from the hood platform 171 above the opening 173. A pivotal closure 174 is pivotally supported at 175 in the passage 177 of the hood assembly 170. The pivotal closure 174 includes a closure surface 176 that is moveable between a closed position, as shown in FIG. 14, and an open position, similar to the closure surface 79 of the previous embodiment. The pivotal closure 174 further includes an extension surface 179 which extends from the closure surface 176 and further limits access into the interior of the disposable container 51. While a pivotal closure 174 is illustrated in the present embodiment, the hood assembly 170 may include other means for limiting access through the passage 177, as explained above in conjunction with the previous embodiment.

The hood assembly 170 has a support contact surface 178 configured to contact and support the hood assembly 170 relative to a shelf 159 extending inward on each of the lateral walls of the enclosure main body 153. The support contact surface 178 of the present invention is illustrated as a skirt depending from the hood platform 171, but other structures, including direct contact by the hood platform 171, may also be utilized. As shown in FIG. 14, once the hood assembly 170 is positioned on the shelves 159 and the door 158 is closed, the hood assembly 170 is retainer between the shelves 159, the cowl 154 and the upper portion of the door 158. The medical waste disposal system 150 is ready for use and sharps or the like may be disposed in the disposable container 51 by placing the items into the hood passage 177 and pivoting the pivotal closure 174, either manually or automatically due to the weight of the item.

Once the disposable container 51 is filled to a given level, a lid 180 is configured to cover and substantially seal the open end 53 of the disposable container 51. A preferred lid 180 is illustrated in FIG. 13 with its underside facing upward in the figure. The lid 180 includes a planar body 181 with a wall 183 depending from three of its edges. The rear edge 185 is substantially open except for a reduced height projection 187 extending therefrom. The lid 180 configuration allows the lid 180 to be slid horizontally onto the disposable container 51 with the projection snapping over the rim 54 as it passes over such.

To facilitate placement of the lid 180 on the disposable container 51, the enclosure door 158 includes a lid slot 161 extending substantially across its width at the height of the container rim 54. A slot door 160 is preferably positioned over the lid slot 161 and connected to the door 158 via hinges 162. A handle 164 may be provided on the slot door 160 to facilitate opening thereof. When the disposable container is full, the slot door 160 is opened, see FIG. 14, and the lid 180 is slid through the lid slot 161 and onto the rim 54 of the disposable container 51. The projection 187 snaps over the front portion of the rim 54 and then finally snaps over the rear portion of the rim 54 to lock the lid 180 on the disposable container 51, as shown in FIG. 15. Once the lid 180 has been positioned, the enclosure door 158 can be opened to remove the covered disposable container 51, which can be disposed of in a normal manner. The is significant amount of material of the hood assembly 170 is not disposed of, but instead, the hood assembly 170 remains supported on the shelves 159 where it can be reused. When it is time to sterilize or otherwise clean the hood assembly, as described in more detail hereinafter, the hood assembly 170 can be slid from the enclosure 152 when the door 158 is opened. Again, reusing of the hood assembly 170 reduces the amount of waste and also reduces the manufacturing costs as a new receptacle 51 can be used with the already manufactured hood assembly 170.

Figure 16:
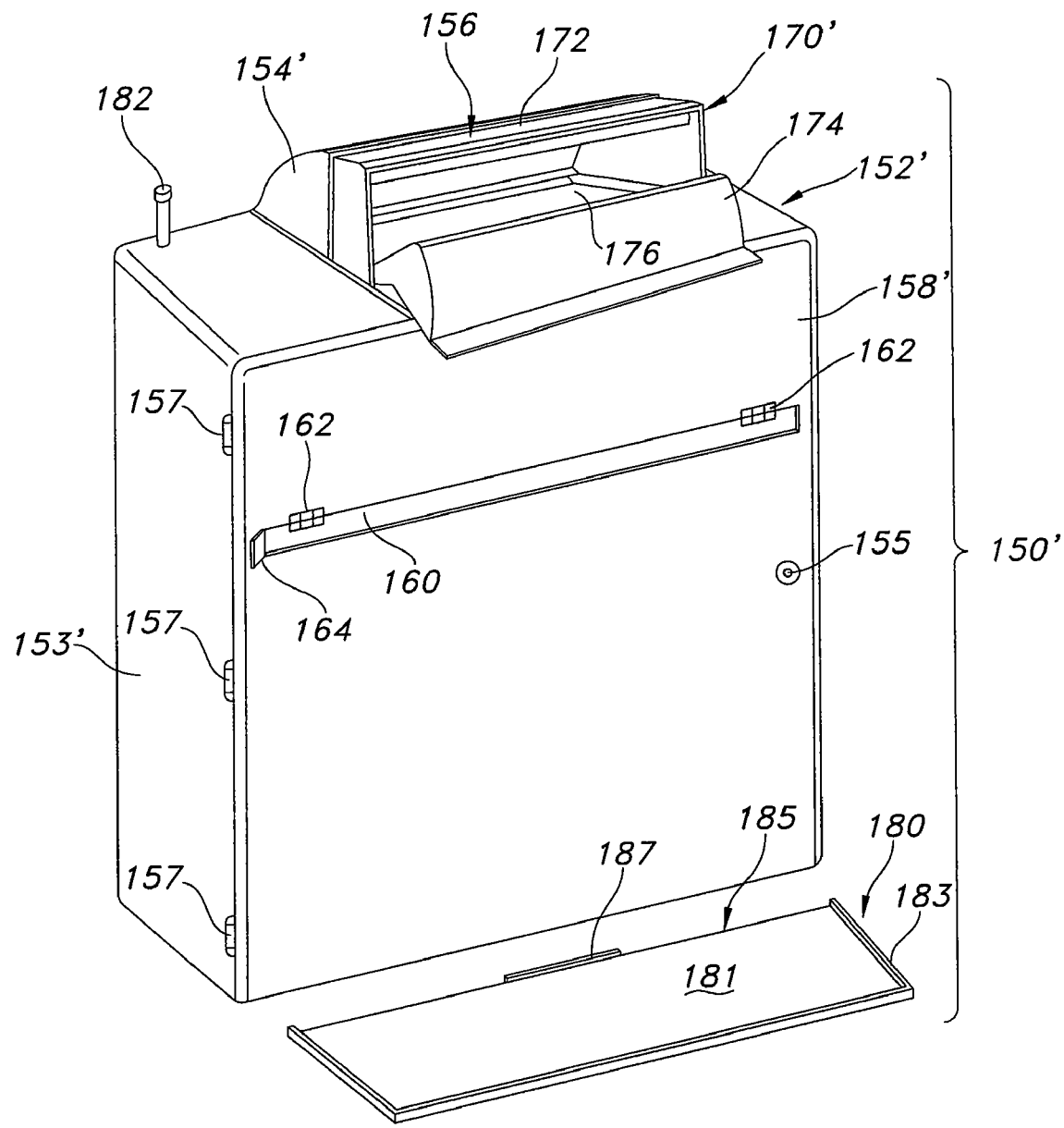
FIG. 16 is an isometric view of a medical waste disposal system that is another alternative exemplary embodiment.
Figure 17:
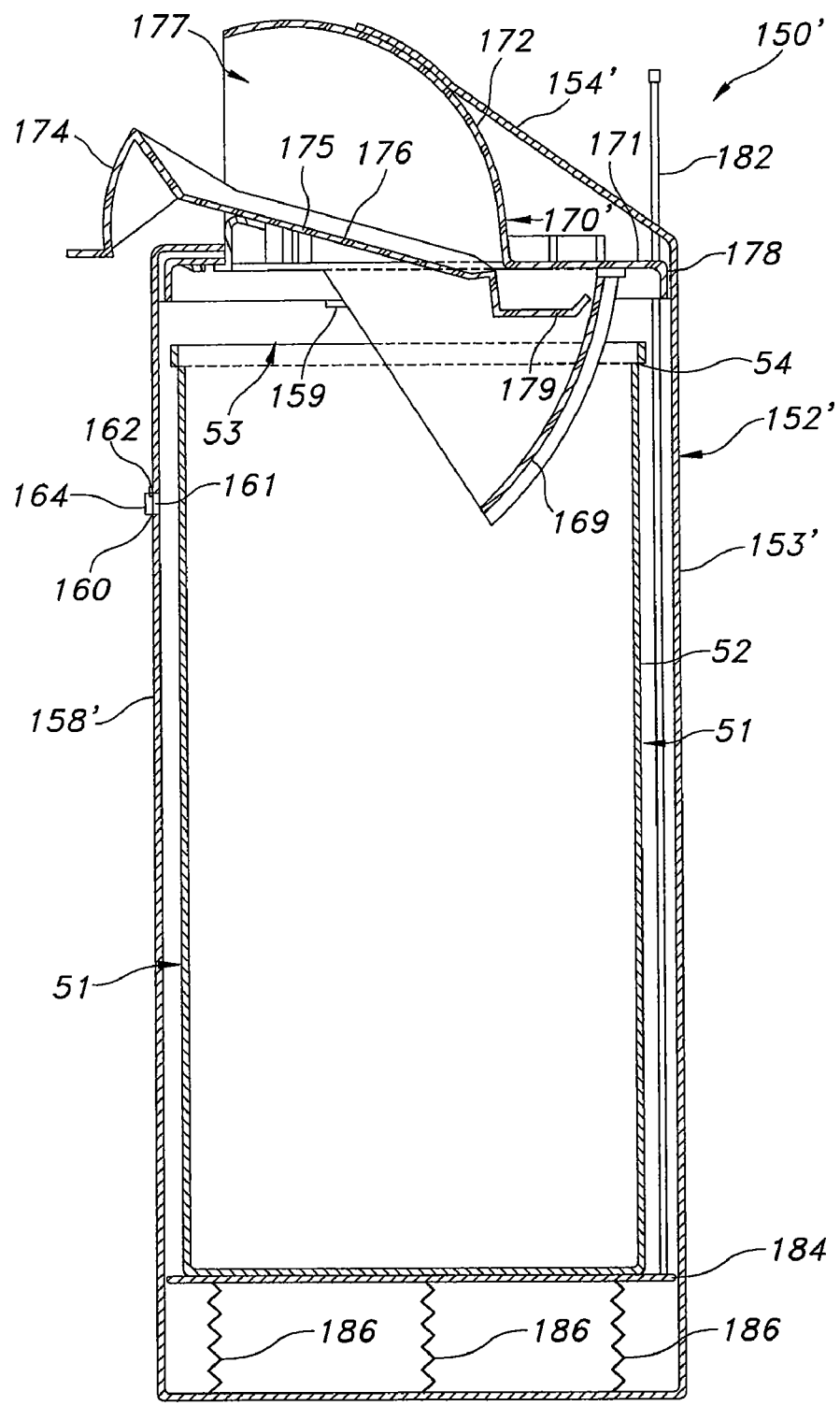
FIG. 17 is a side cross-sectional view of the medical waste disposal system of FIG. 16 with the disposable container in a fill position.
Figure 18:
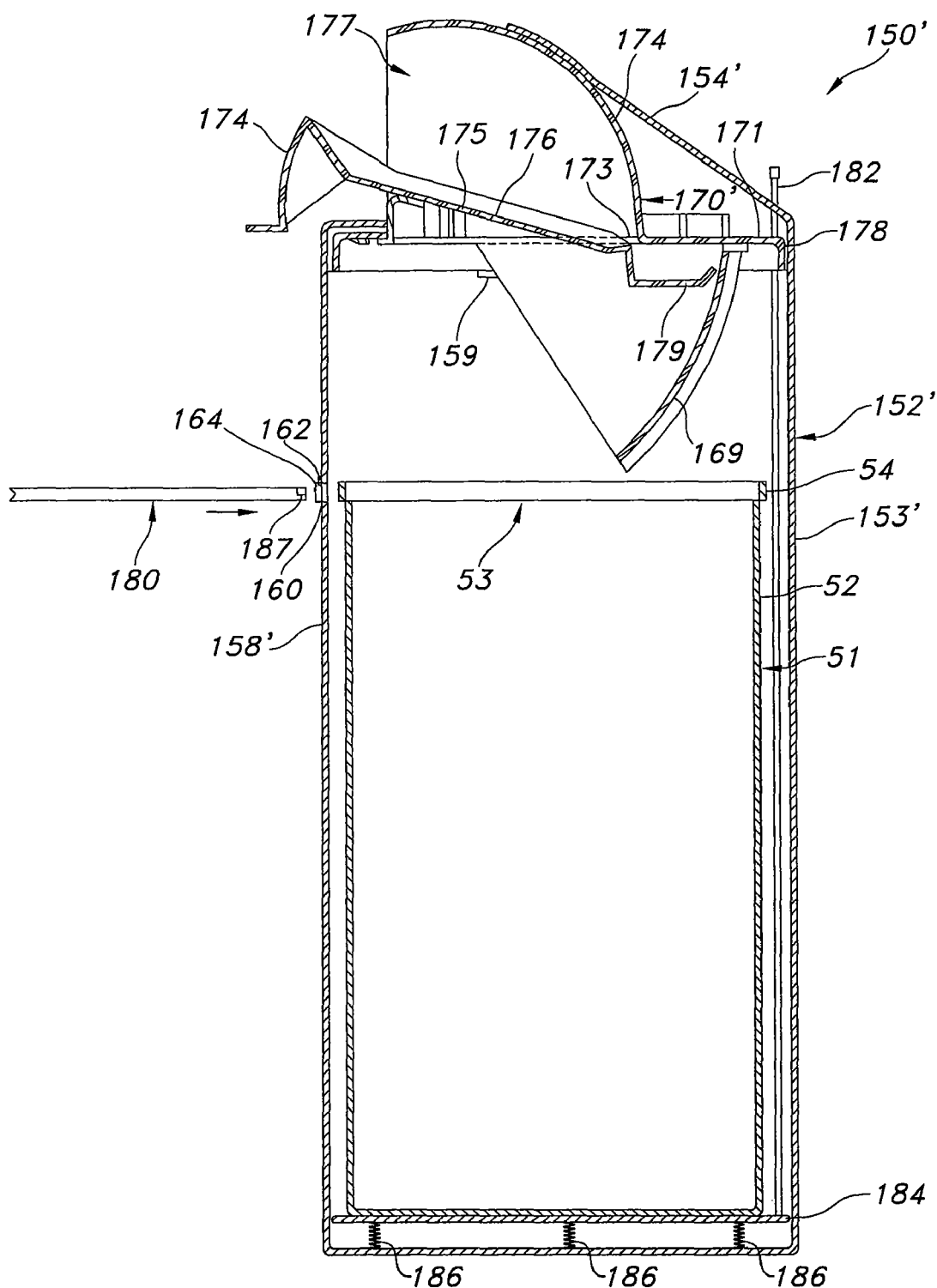
FIG. 18 is a side cross-sectional view similar to FIG. 17 with the disposable container in a cover position.

Referring to FIGS. 16-18, a medical waste disposal system 150' in accordance with another alternative embodiment will be described. The system 150' is similar to the previous embodiment and generally comprises a hollow, outer enclosure 152', a disposable container 51 configured to be located within the outer enclosure 152, and a reusable hood assembly 170'. The hood assembly 170' is generally the same as in the previous embodiment and like elements are numbered alike. The hood assembly 170' differs from the hood assembly 170 of the previous embodiment in that it further includes a fixed cowl surface 169 extending downward from the hood platform 171. In the operable position shown in FIG. 17, the cowl surface 169 extends into the interior of the disposable container 51.

In the position illustrated in FIG. 17, the cowl surface 169 would prevent a lid 180 from being slid over the container rim 54. To facilitate covering of the container opening 53, the disposable container 51 is positioned on a moveable platform 184. Springs 186 or the like bias the platform 184 to the operable position shown in FIG. 17. Once the disposable container 51 is filled, a push rod 182 is used to move the platform 184 against the spring bias to the position shown in FIG. 18 such that the rim 54 of the disposable container 51 is clear of the cowl surface 169 and the container 51 is positioned to receive the lid 180. Similar to the previous embodiment, a lid slot 161 extends through the enclosure door 158'. The lid slot 161 is positioned lower relative to the top of the door 158' such that the lid slot 161 aligns with the container rim 54 when the disposable container 51 is lowered to the position shown in FIG. 18. The slot door 160 is opened and the lid 180 is slid over the container rim 54 in the manner described with respect to the previous embodiment.

Again, once the lid 180 has been positioned, the enclosure door 158' can be opened to remove the covered disposable container 51, which can be disposed of in a normal manner. The significant amount of material of the hood assembly 170', including cowl surface 169, is not disposed of, but instead, the hood assembly 170' remains supported on the shelves 159 where it can be reused. When it is time to sterilize or otherwise clean the hood assembly, as described in more detail hereinafter, the hood assembly 170' can be slid from the enclosure 152' when the door 158' is opened. Again, reusing of the hood assembly 170' reduces the amount of waste and also reduces the manufacturing costs as a new receptacle 51 can be used with the already manufactured hood assembly 170'.

Figure 19:
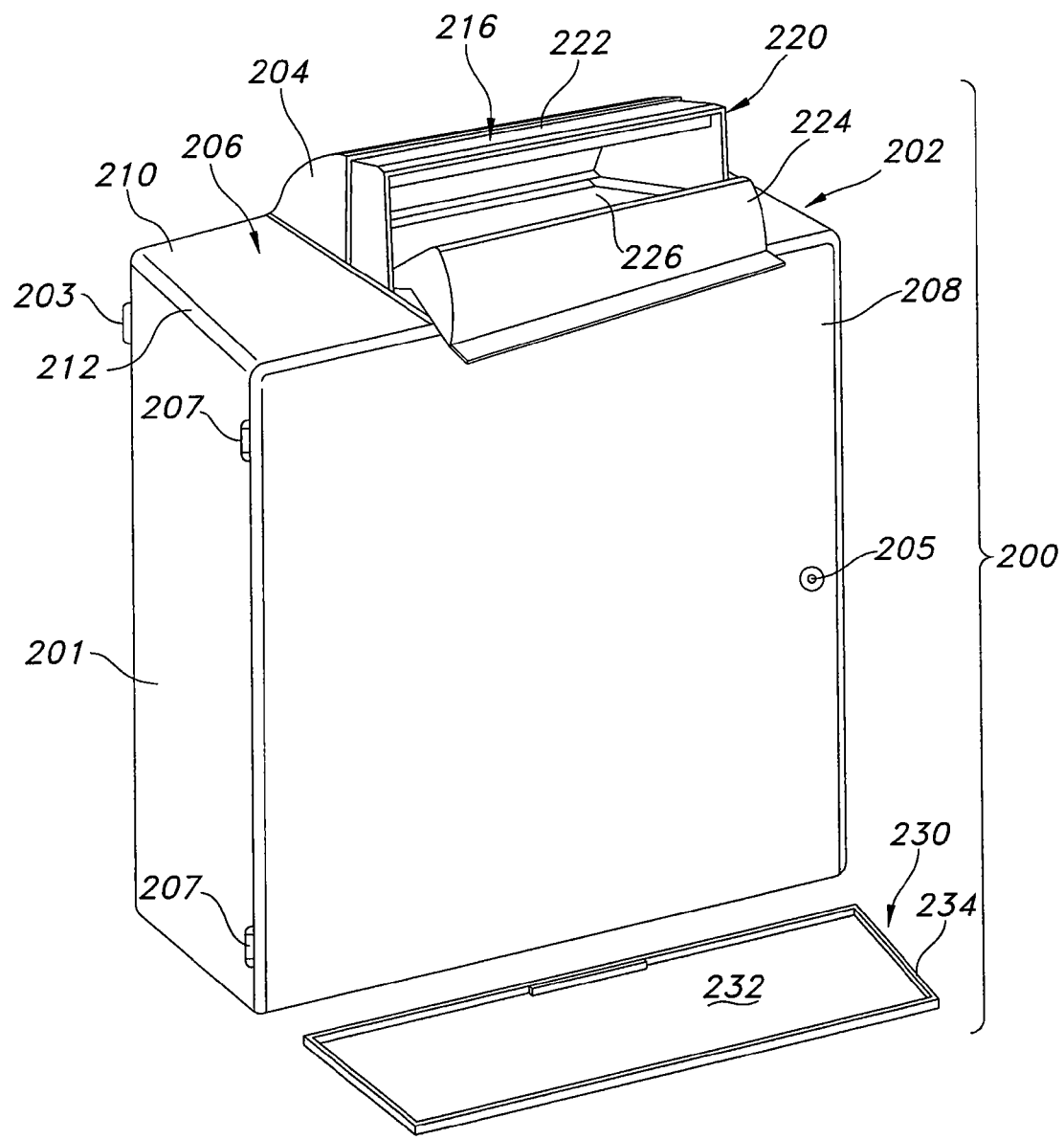
FIG. 19 is an isometric view of a medical waste disposal system that is another alternative exemplary embodiment.
Figure 20:
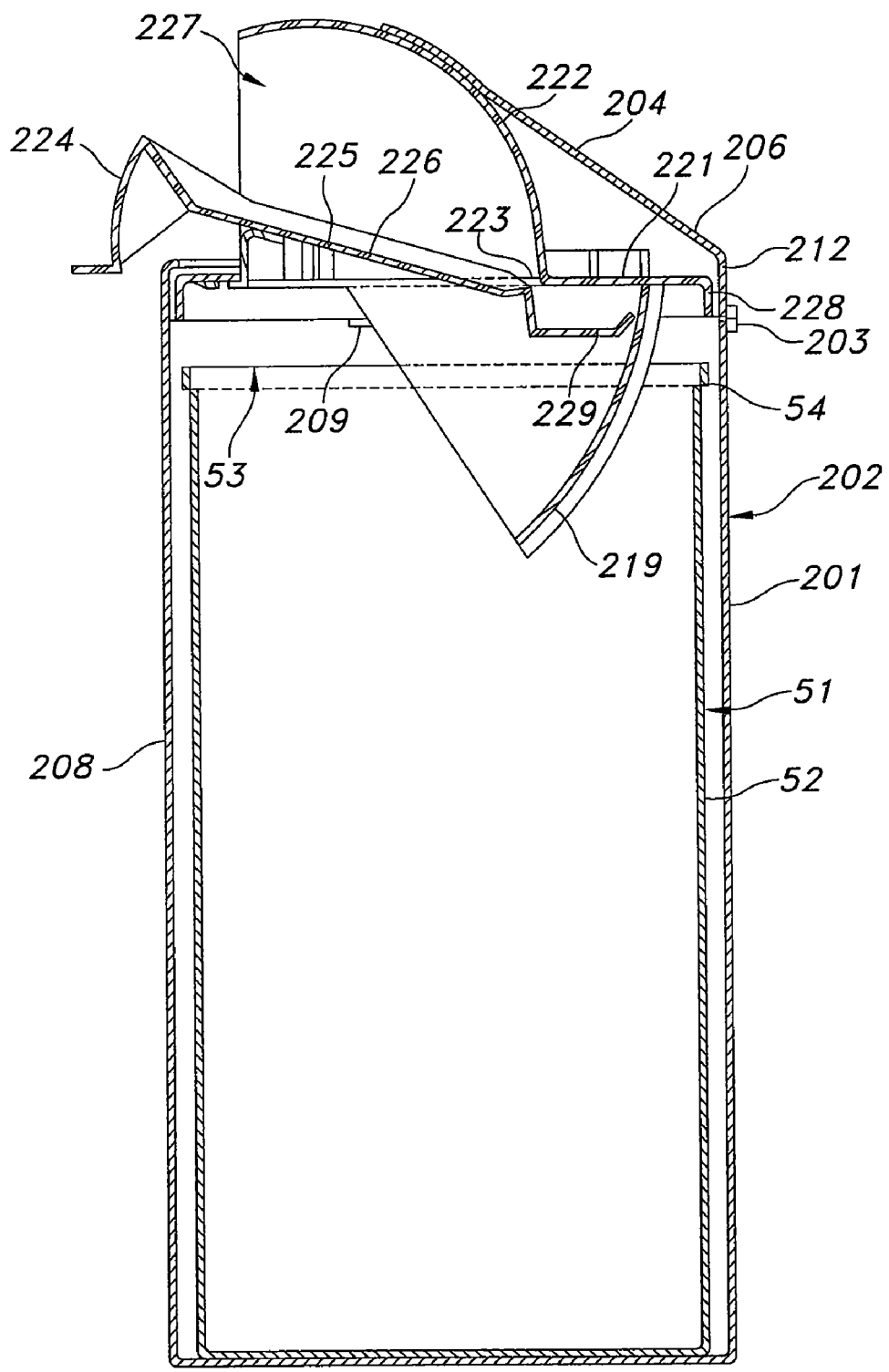
FIG. 20 is a side cross-sectional view of the medical waste disposal system of FIG. 18 with the hood assembly in a fill position.
Figure 21:
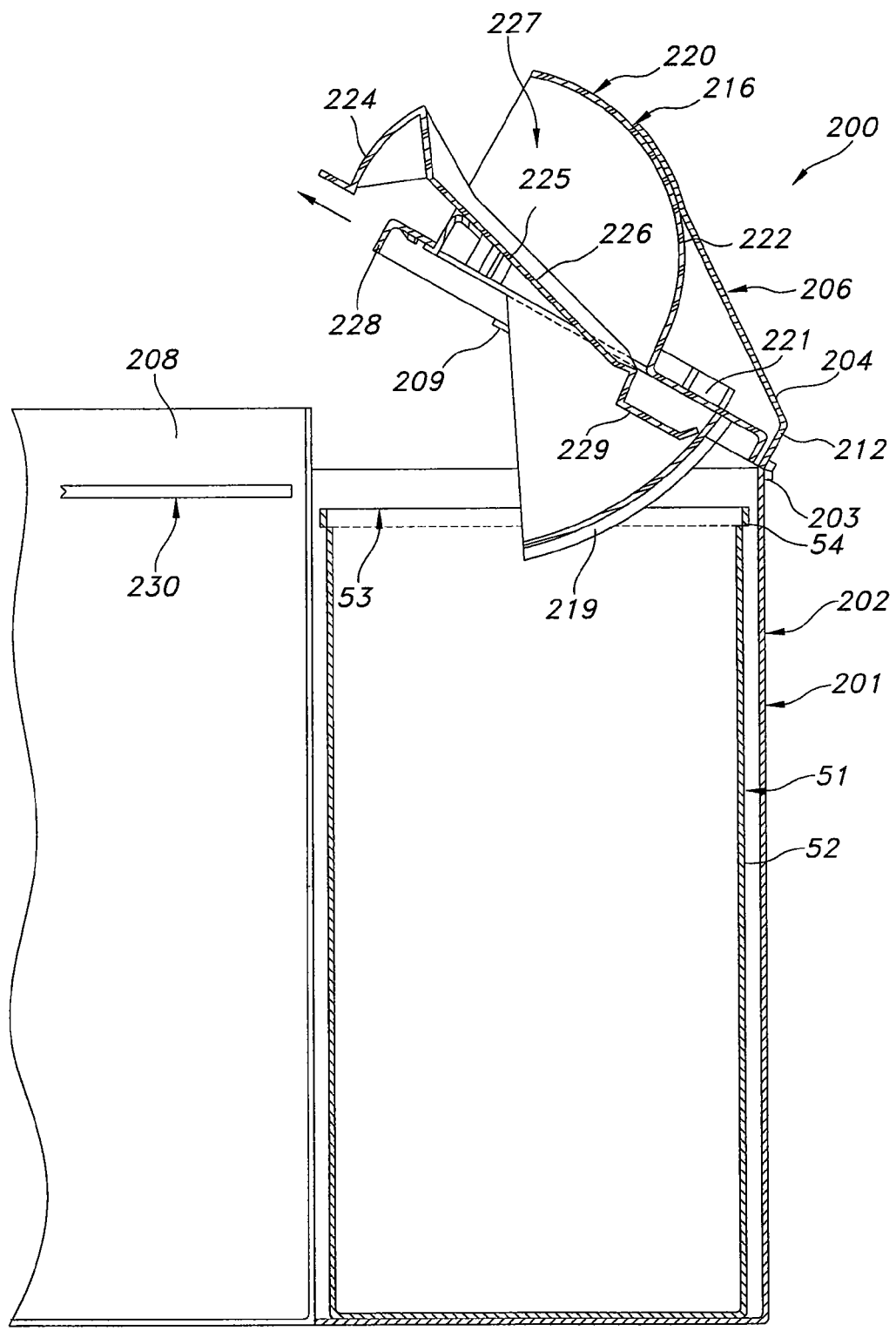
FIG. 21 is a side cross-sectional view similar to FIG. 20 with the hood assembly in a cover position.

Referring to FIGS. 19-21, a medical waste disposal system 200 in accordance with another alternative embodiment will be described. The system 200 generally comprises a hollow, outer enclosure 202, a disposable container 51 configured to be located within the outer enclosure 152, and a reusable hood assembly 170. The disposable container 51 is substantially the same as in the previous embodiments and includes a wall structure 52 that defines an open end 53 with a rim 54 thereabout. The disposable container 51 is configured to receive medical waste, including sharps and the like, and may have various configurations of the wall structure 52 and the rim 54 other than the illustrated structure.

Turning to the outer enclosure 202, the enclosure 202 includes a main body comprising a lower main body 201 and an upper main body 206. The upper main body 206 includes a generally planar upper surface 210 with side and rear walls 212 depending therefrom. The upper main body 206 also includes a raised cowl 204 extending from the upper surface 210 over a slot 216. While an external raised cowl 204 is illustrated, such is not required as the hood assembly cowl 222 may provide the only cowl with the top surface 210 of the enclosure 202 being substantially flat. Referring to FIGS. 20 and 21, the upper main body 206 includes opposed shelves 209 extending inward from the side walls 212. Similar to the previous embodiment, the shelves 209 are configured to support the hood assembly 220. The upper main body 206 is hinged to the lower main body 201 along a rear edge thereof via hinges 203. Since the hood assembly 220 is supported by the upper main body 206, the hood assembly 220 pivots with the upper main body 206, as illustrated in FIG. 21.

An access door 208 is secured by hinges 207 onto the lower main body 201 of the enclosure 202. Opposite the hinges 207, the door 208 includes a lock 205 to lock the door 208 in a closed position relative to the lower main body 201. To position a disposable container 51 within the enclosure 202, the door 208 is opened and the upper main body 206, and thereby the hood assembly 220, is pivoted to the position illustrated in FIG. 21. After the disposable container 51 is positioned in the enclosure 202, the upper main body 206 is pivoted to the position illustrated in FIG. 20 such that the hood assembly 220 overlies the open end 53 of the disposable container 51 and defines a tortuous path or the like through the hood assembly 220 into the disposable container 51. The door 208 is locked relative to the lower main body 201 such that the disposable container 51 and the hood assembly 220 are restrained within the enclosure 202.

Figure 22:
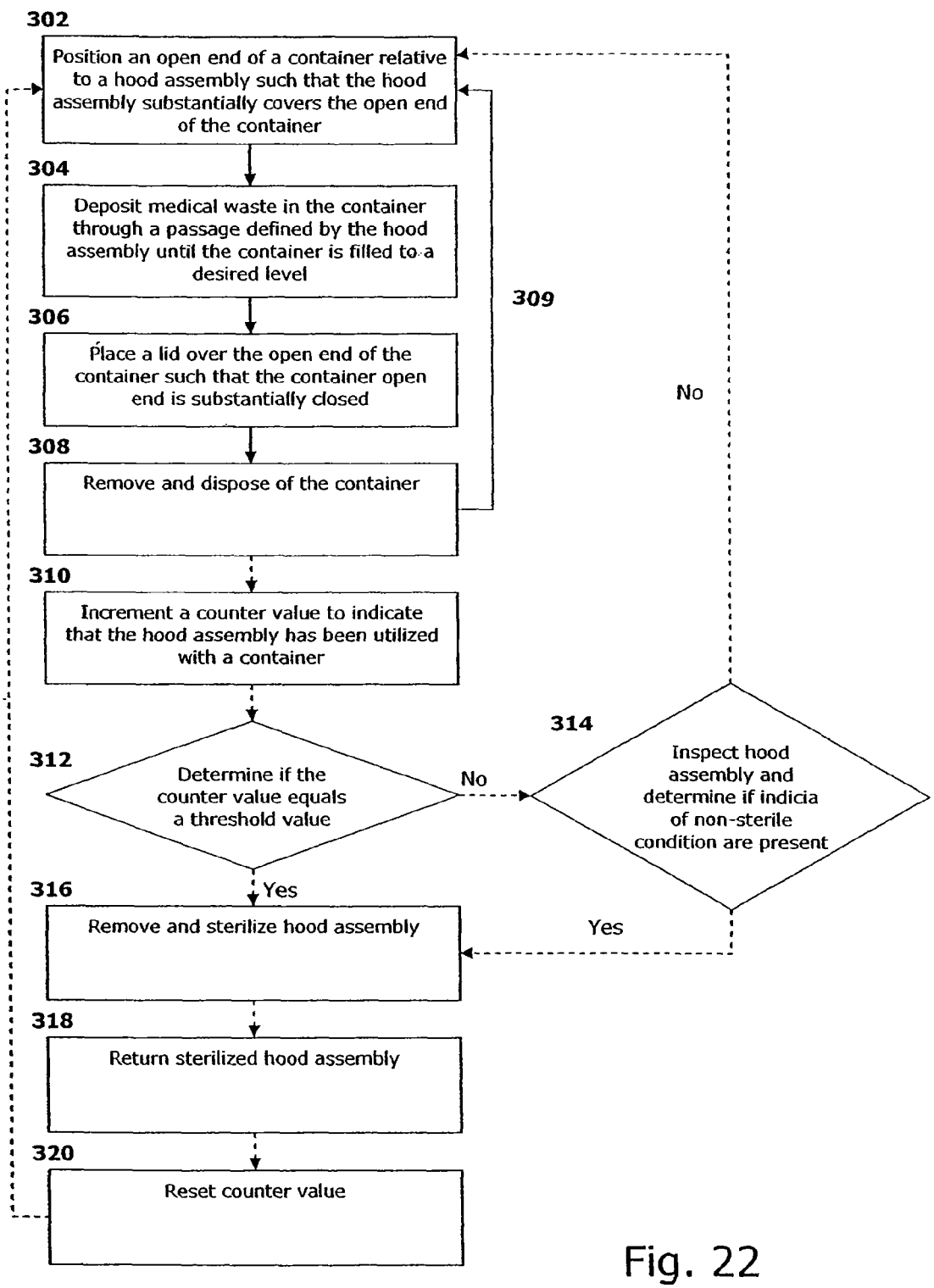
FIG. 22 is a schematic diagram illustrating an exemplary method in accordance with at least one embodiment of the present invention.

Referring to FIGS. 21 and 22, the hood assembly 220 includes a hood platform 221 with a opening 223 therethrough. A raised cowl 222 extends from the hood platform 221 above the opening 223. A pivotal closure 224 is pivotally supported at 225 in the passage 227 of the hood assembly 220. The pivotal closure 224 includes a closure surface 226 that is moveable between a closed position, as shown in FIG. 20, and an open position, similar to the closure surface 176 of the previous embodiment. The pivotal closure 224 further includes an extension surface 229 which extends from the closure surface 226 and further limits access into the interior of the disposable container 51. The hood assembly 220 further includes a fixed cowl surface 219 extending downward from the hood platform 221. In the operable position shown in FIG. 20, the cowl surface 219 extends into the interior of the disposable container 51. While a pivotal closure 224 with a depending cowl surface 219 is illustrated in the present embodiment, the hood assembly 220 may include other means for limiting access through the passage 227, as explained above in conjunction with the previous embodiments.

The hood assembly 220 has a support contact surface 228 configured to contact and support the hood assembly 220 relative to the shelves 209 extending inward on each of the side walls 212 of the upper main body 206. The support contact surface 228 of the present invention is illustrated as a skirt depending from the hood platform 221, but other structures, including direct contact by the hood platform 221, may also be utilized. As shown in FIG. 20, once the hood assembly 220 is positioned on the shelves 209 and the door 208 is closed, the hood assembly 220 is retained between the shelves 209, the cowl 204 and the upper portion of the door 208. The medical waste disposal system 200 is ready for use and sharps or the like may be disposed in the disposable container 51 by placing the items into the hood passage 227 and pivoting the pivotal closure 224, either manually or automatically due to the weight of the item.

Once the disposable container 51 is filled to a given level, a lid 230 is configured to cover and substantially seal the open end 53 of the disposable container. A preferred lid 230 is illustrated in FIG. 19 with its underside facing upward in the figure. The lid 230 includes a planar body 232 with a wall 234 depending from its complete perimeter. A secondary protrusion 236 extends from the planar body 232 adjacent the rear portion of the wall 234 and is configured such that the rear portion of the container rim 54 will be received between the rear portion of the wall 234 and the protrusion 236. The lid 230 is configured to be placed on the disposable container 51 and does not require a sliding configuration.

To facilitate placement of the lid 230 onto a filled disposable container 51, the enclosure door 208 is opened and the upper main body 206, and thereby the hood assembly 220, is pivoted to the raised position illustrated in FIG. 21. Raising of the hood assembly 220 removes the cowl surface 219 from the disposable container 51 such that the lid 230 may be placed thereon. The cowl surface 219 is preferably distanced from the rim 54 such that the lid 230 can be placed over and then lowered onto the container rim 54. However, a sliding lid, as in the previous embodiments, or other lid configurations may also be utilized. Once the lid 230 has been positioned, the covered disposable container 51 can be removed from the enclosure 202 and disposed of in a normal manner. The significant amount of material of the hood assembly 220 is not disposed of, but instead, the hood assembly 220 remains supported on the shelves 209 where it can be reused. When it is time to sterilize or otherwise clean the hood assembly 220, as described in more detail hereinafter, the hood assembly 220 can be slid from the upper main body 206 when the door 208 is open. Again, reusing of the hood assembly 220 reduces the amount of waste and also reduces the manufacturing costs as a new receptacle 51 can be used with the already manufactured hood assembly 220.

Referring to FIG. 22, a method of medical waste disposal incorporating reusable hood assemblies will be described. The method starts at step 302 with the positioning of the open end of a container relative to a hood assembly such that the hood assembly substantially covers the container open end. As illustrated above, the hood assembly may have various configurations and may incorporate various components, including pivoting components, fixed components or a combination thereof, to define the passage. The hood assembly is not limited to the embodiments illustrated herein. The method incorporates any of various structures and assemblies for positioning the disposable container relative to the hood assembly.

In step 304, medical waste is deposited into the container through a passage defined by the hood assembly until the container is filled to a desired level.

Once the container is filled to a desired level, a lid is placed over the container open end such that the container open end is substantially closed, as indicated at step 306. As discussed above, step 306 may be performed while the hood assembly is still covering the container open end or when the container open end is enclosed within an outer enclosure. Alternatively, step 306 may be performed after the container open end has been exposed.

In step 308, the substantially closed disposable container is removed and disposed of in a normal manner. In one exemplary embodiment of the method, the process next repeats, as indicated by arrow 309, to step 302.

In another exemplary embodiment of the method, at step 310 a counter value is incremented to indicate that the hood assembly has been utilized with a container. The counter value may be maintained in a physical location, for example, in a log book or on a computer, or the counter value may be remembered by the operator(s). Any system can be utilized to track the number of times the hood assembly has been utilized.

In step 312, the counter valve is checked to determine if a threshold value has been reached. The threshold value can be any value of one or more. The threshold value represents the number of container fillings the operator allows between sterilization of the hood assembly. If the counter value is at the threshold value, it is time to sterilize the hood assembly and the method proceeds to step 316, as described in more detail hereinafter.

If the counter value is less than the threshold value, the method proceeds to step 314 wherein an inspection is made to determine if there is a presence of any indicia on the hood assembly of a non-sterile condition. The indicia may include, for example, but not limited to, fluid presence, excessive odor, or the presence of dried foreign material or stains. Such determination is subjective to the operator. If it is determined that no such indicia is present, the hood assembly may be reused and the method proceeds back to step 302. If it is determined that such indicia is present on the hood assembly, the hood assembly is removed and the method proceeds to step 316.

Step 316 provides for the sterilization of the hood assembly. Various methods and devices exist for the sterilization, decontamination, or disinfection of the hood assembly. These methods include, but are not limited to, heat sterilization (e.g., autoclaving), irradiation (e.g., ultraviolet or ionizing irradiation), gas sterilization (e.g., using ethylene oxide), photosensitization, membrane sterilization, or the use of chemical disinfectants (formaldehyde, glutaraldehyde, alcohols, mercury compounds, quaternary ammonium compounds, halogenated compounds, solvent/detergent systems, or peroxides). Sterilization may be performed at the operator's location or may be done offsite.

Once the hood assembly has been sterilized, step 318 provides that the hood assembly be returned and step 320 provides that the counter value be reset to its initial value. Thereafter, the procedure begins again at step 302. In step 318, the sterilized hood assembly may be returned directly into operation, or may be returned to a queue of sterilized hood assemblies, such that an alternate sterilized hood assembly can be utilized while the first hood assembly is being sterilized. Such a system of at least two hood assemblies minimizes downtime for the operator.

In typical prior art systems, the hood assembly is permanently affixed to the disposable container, serves to permanently close the container upon filling thereof, and is disposed with the disposable container. In contrast to such typical systems, exemplary embodiments of container systems disclosed herein make it possible to reuse portions of the container system while facilitating safe and secure disposal of medical waste, thus reducing waste and cost. Though each of the exemplary container system embodiments disclosed herein can optionally be configured for complete disposal of all or substantially all of its components together (e.g., with a hood assembly permanently affixed to the disposal container, permanently closing the container, and/or disposed of with the container), it is preferred at least one component (e.g., the hood assembly) of the container system be reusable with disposable components (e.g., the container) to reduce costs and waste.

In another exemplary embodiment of the container system disclosed herein, the container system is provided as part of a kit for medical waste disposal. The kit includes a plurality of containers and a hood assembly configured to substantially cover an open end of each said container. The hood assembly can have various configurations including, but not limited to, those described above. The hood assembly defines a passage through which medical waste can be passed to the open end of said container. The kit further includes a plurality of lids, separate from the hood assembly, each configured to be placed over the open end of each said container and to substantially close the open end of said container when said container is at least partially filled with medical waste. Each container is configured for separation from the hood assembly for disposal.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A kit for medical waste disposal comprising:
   a plurality of containers;
   a hood assembly configured to substantially cover an open end of one of said containers, the hood assembly defining a passage through which medical waste can be passed to the open end of the one container; and
   a plurality of lids, separate from the hood assembly, each configured to be placed over an open end of a respective container and to substantially close the open end of the respective container when the respective container is at least partially filled with medical waste;
   the one container being configured for separation from the hood assembly for disposal; and
   wherein the hood assembly and the containers are retained in an external enclosure having an access door with a lid slot therethrough for placing a respective lid on a respective container.

2. The kit of claim 1 wherein a deck component is configured to be positioned over a respective container open end, and wherein the deck component includes first and second connectors with the hood assembly connected to the deck component via the first connectors and the lid is positioned into engagement with the second connectors.

3. A kit for medical waste disposal comprising:
   a plurality of containers;
   a hood assembly configured to substantially cover an open end of one container, the hood assembly defining a passage through which medical waste can be passed to the open end of the one container; and
   a plurality of lids, separate from the hood assembly, each lid configured to be placed over an open end of a respective container and to substantially close the open end when the respective container is at least partially filled with medical waste;
   the one container being configured for separation from the hood assembly for disposal, the hood assembly and the containers being retained in an external enclosure, the external enclosure having an upper body pivotal relative to a lower body and wherein the one container is positioned in the lower body and the hood assembly is supported by the upper body such that the hood assembly is pivotal relative to the one container and wherein the external enclosure further comprises an access door securable relative to the upper and lower bodies such that the hood assembly and the container are secured at least partially within the enclosure when the door is secured.

4. The kit of claim 1 wherein each container includes a substantially planar deck surface about the open end and wherein the hood assembly is configured to be removably secured to the planar deck surface.

5. The kit of claim 4 wherein the lid is pivotally attached to the planar deck surface.

6. The kit of claim 1 including at least two hood assemblies.

7. The kit of claim 3 wherein each container includes a substantially planar deck surface about the open end and wherein the hood assembly is configured to be removably secured to the planar deck surface.

8. The kit of claim 7 wherein the lid is pivotally attached to the planar deck surface.

9. The kit of claim 3 including at least two hood assemblies.

10. A kit for medical waste disposal, which comprises:
    a container having an open end;
    a hood mountable over the open end of the container, the hood defining a passage through which medical waste may be passed for deposit within the open end of the container;
    a lid dimensioned and adapted to be mounted adjacent the open end of the container to substantially close the open end while the hood is mounted over the open end of the container, the lid being movable independent of the hood; and
    an enclosure for at least partially enclosing the container, the enclosure including at least one lid slot dimensioned and adapted to permit passage of one lid for mounting adjacent the open end of the container.

11. The kit of claim 10 wherein the hood is dimensioned and adapted to be separable from the container.

12. The kit of claim 11 including a plurality of containers, each container having an open end.

13. The kit of claim 12 wherein each container includes a hood mountable adjacent the open end thereof.

14. The kit of claim 13 including a plurality of lids, each lid dimensioned and adapted to be mounted adjacent the open end of one container to substantially close the open end when the hood is mounted to the one container.

15. The kit of claim 14 wherein the enclosure is dimensioned and adapted to at least partially enclose the containers.

16. The kit of claim 15 wherein the enclosure includes an access door to permit access to the containers.

* * * * *